US 9,113,967 B2

(12) United States Patent
Soubeiran

(10) Patent No.: US 9,113,967 B2
(45) Date of Patent: Aug. 25, 2015

(54) INTRACORPOREAL DEVICE FOR MOVING TISSUE

(76) Inventor: Arnaud Soubeiran, Paris (FR)

( * ) Notice: Subject to any disclaimer, the term of this patent is extended or adjusted under 35 U.S.C. 154(b) by 378 days.

(21) Appl. No.: 13/395,040

(22) PCT Filed: Sep. 7, 2010

(86) PCT No.: PCT/FR2010/000608
§ 371 (c)(1),
(2), (4) Date: Mar. 8, 2012

(87) PCT Pub. No.: WO2011/030015
PCT Pub. Date: Mar. 17, 2011

(65) Prior Publication Data
US 2012/0179215 A1 Jul. 12, 2012

(30) Foreign Application Priority Data
Sep. 9, 2009 (FR) ...................................... 09 04306

(51) Int. Cl.
A61B 17/72 (2006.01)
A61B 17/70 (2006.01)
(Continued)

(52) U.S. Cl.
CPC .......... A61B 17/7216 (2013.01); A61B 17/7014 (2013.01); A61B 17/8004 (2013.01); A61B 17/8076 (2013.01); A61F 2002/30706 (2013.01); A61F 2250/0082 (2013.01)

(58) Field of Classification Search
CPC .................................................... A61B 17/7216
USPC ............................................ 606/63, 68, 258
See application file for complete search history.

(56) References Cited

U.S. PATENT DOCUMENTS 2,672,861 A 3/1954 Jonas et al.
5,074,882 A * 12/1991 Grammont et al. ............. 606/63
(Continued)

FOREIGN PATENT DOCUMENTS

DE 85 15 687 U1 10/1985
FR 2267080 A1 11/1975
(Continued)

OTHER PUBLICATIONS

Foster et al., The Spine Journal, pp. 682-694, 2005 (abstract).
(Continued)

Primary Examiner — David Bates
(74) Attorney, Agent, or Firm — Peter K. Sollins; Foley Hoag LLP

(57) ABSTRACT

A device for moving tissue inside the body, in particular bone tissue, may include a reference part, a transport part which is slidably mounted relative to the reference part; a threaded rod pivotably mounted relative to the reference part, a control shaft, driving means connecting the control shaft to the threaded rod, a connecting nut between the transport part and the threaded rod, the connecting nut being mounted onto the threaded rod and being rotatably guided relative to the reference part, and means for converting the movement of the connecting nut along the threaded rod into a movement of the transport part relative to the reference part. In order to limit the longitudinal translation of said threaded rod relative to the reference part, a first abutment and a second abutment rigidly connected to the threaded rod respectively cooperate with a first bearing and a second bearing, these bearings being rigidly connected to the reference part and being placed at a distance from one another between the abutments. The connecting nut is movable along the threaded rod between the first bearing and second bearing.

12 Claims, 16 Drawing Sheets

(51) Int. Cl.
*A61B 17/80* (2006.01)
*A61F 2/30* (2006.01)

(56) References Cited

U.S. PATENT DOCUMENTS

| | | | |
|---|---|---|---|
| 5,112,333 A | 5/1992 | Fixel | |
| 5,263,955 A * | 11/1993 | Baumgart et al. | 606/63 |
| 5,350,379 A | 9/1994 | Spievack | |
| 5,505,733 A * | 4/1996 | Justin et al. | 606/63 |
| 5,534,004 A | 7/1996 | Santangelo | |
| 5,704,939 A | 1/1998 | Justin | |
| 6,336,929 B1 | 1/2002 | Justin | |
| 6,796,984 B2 | 9/2004 | Soubeiran | |
| 6,849,076 B2 | 2/2005 | Blunn et al. | |
| 7,135,022 B2 * | 11/2006 | Kosashvili et al. | 606/63 |
| 7,481,841 B2 | 1/2009 | Hazebrouck et al. | |
| 7,559,951 B2 | 7/2009 | DiSilvestro et al. | |
| 8,137,349 B2 * | 3/2012 | Soubeiran | 606/63 |
| 8,449,543 B2 * | 5/2013 | Pool et al. | 606/63 |
| 8,568,457 B2 * | 10/2013 | Hunziker | 606/258 |
| 8,632,548 B2 * | 1/2014 | Soubeiran | 606/90 |
| 8,663,285 B2 * | 3/2014 | Dall et al. | 606/258 |
| 2005/0246034 A1 | 11/2005 | Soubeiran | |
| 2005/0261779 A1 | 11/2005 | Meyer | |
| 2009/0254088 A1 * | 10/2009 | Soubeiran | 606/63 |
| 2010/0049204 A1 * | 2/2010 | Soubeiran | 606/90 |
| 2010/0280519 A1 | 11/2010 | Soubeiran | |
| 2011/0238126 A1 * | 9/2011 | Soubeiran | 606/86 R |

FOREIGN PATENT DOCUMENTS

| | | |
|---|---|---|
| FR | 2794357 A1 | 12/2000 |
| FR | 2843538 A1 | 2/2004 |
| FR | 2891727 A1 | 4/2007 |
| FR | 2892617 A1 | 5/2007 |
| FR | 2900563 A1 | 11/2007 |
| FR | 2906453 A1 | 4/2008 |
| FR | 2916622 A1 | 12/2008 |
| WO | 95/24870 A1 | 9/1995 |
| WO | 99/51160 A1 | 10/1999 |
| WO | 01/78614 A1 | 10/2001 |
| WO | 02/071962 A1 | 9/2002 |
| WO | 2004/019796 A1 | 3/2004 |
| WO | 2006/010844 A1 | 2/2006 |
| WO | 2007/051924 A1 | 5/2007 |
| WO | 2007/144489 A2 | 12/2007 |

OTHER PUBLICATIONS

International Search Report and Written Opinion for PCT/FR2010/000608, dated Nov. 22, 2010.
Search Report and Written Opinion for FR0904306, dated May 4, 2010.

* cited by examiner

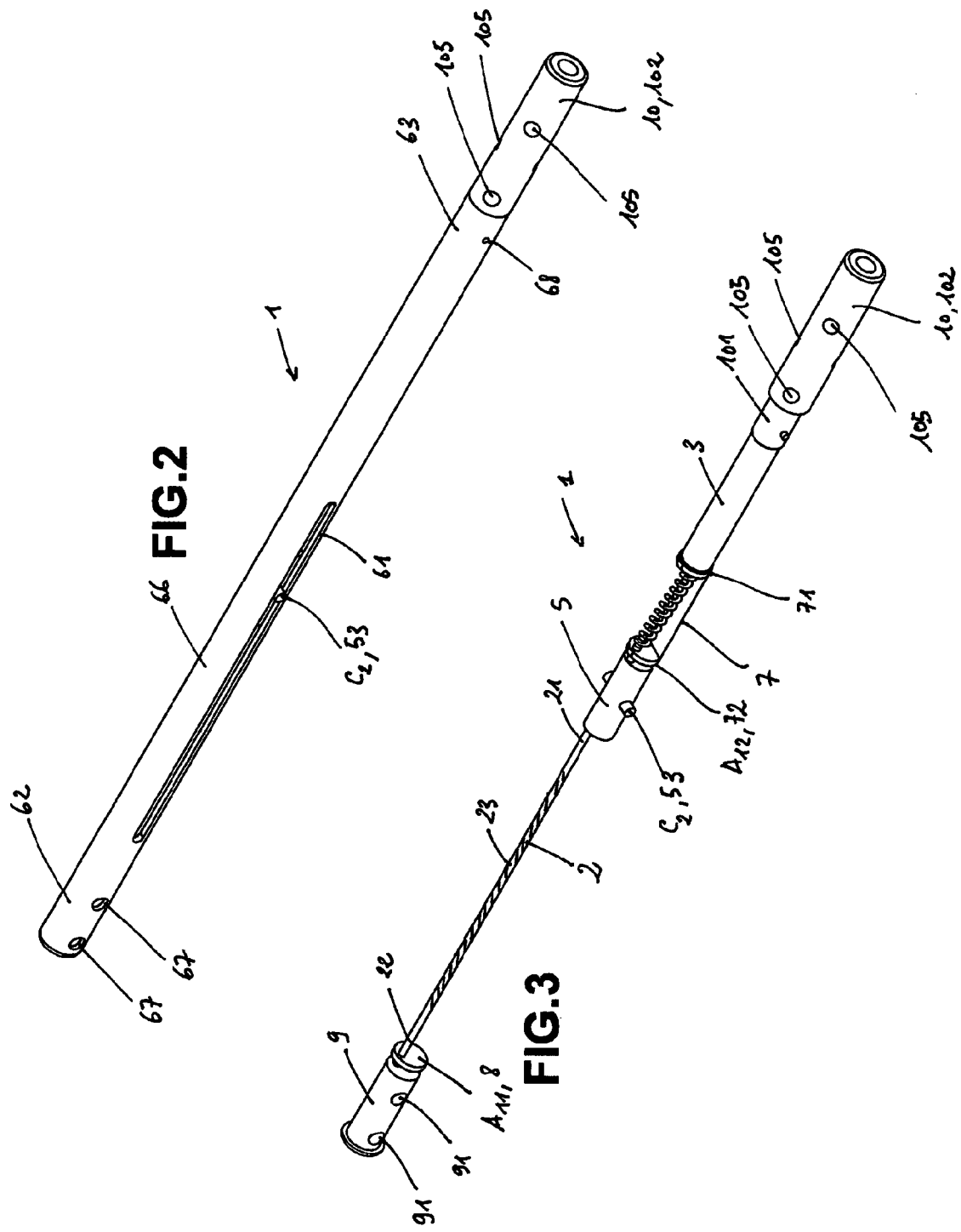

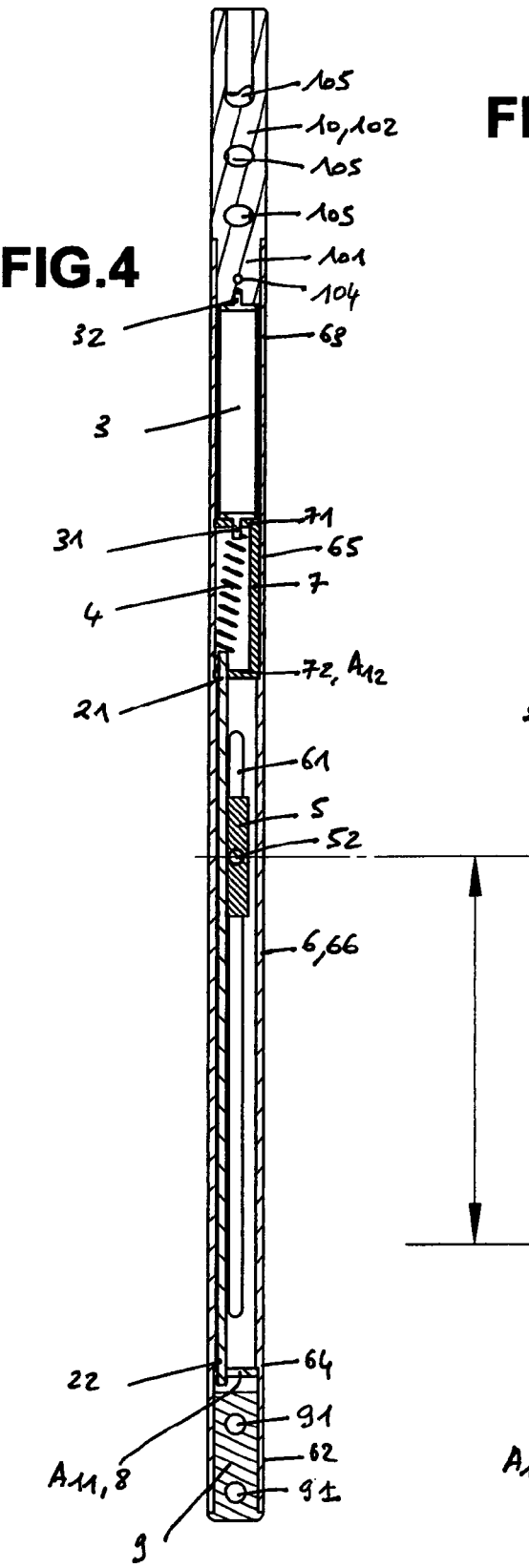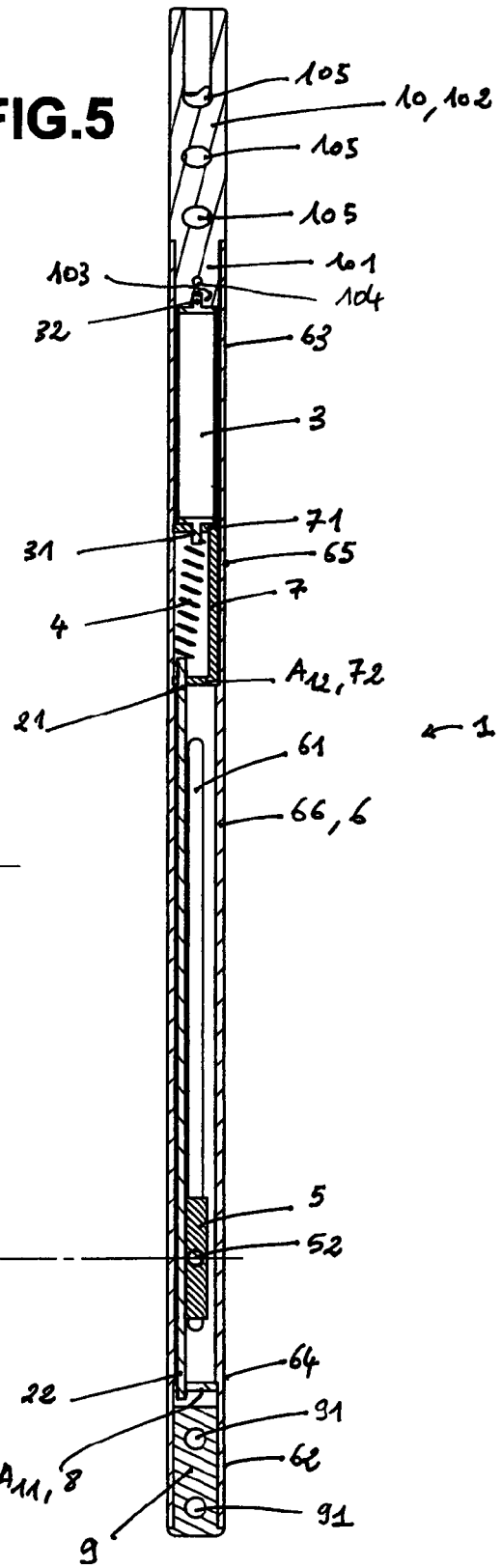

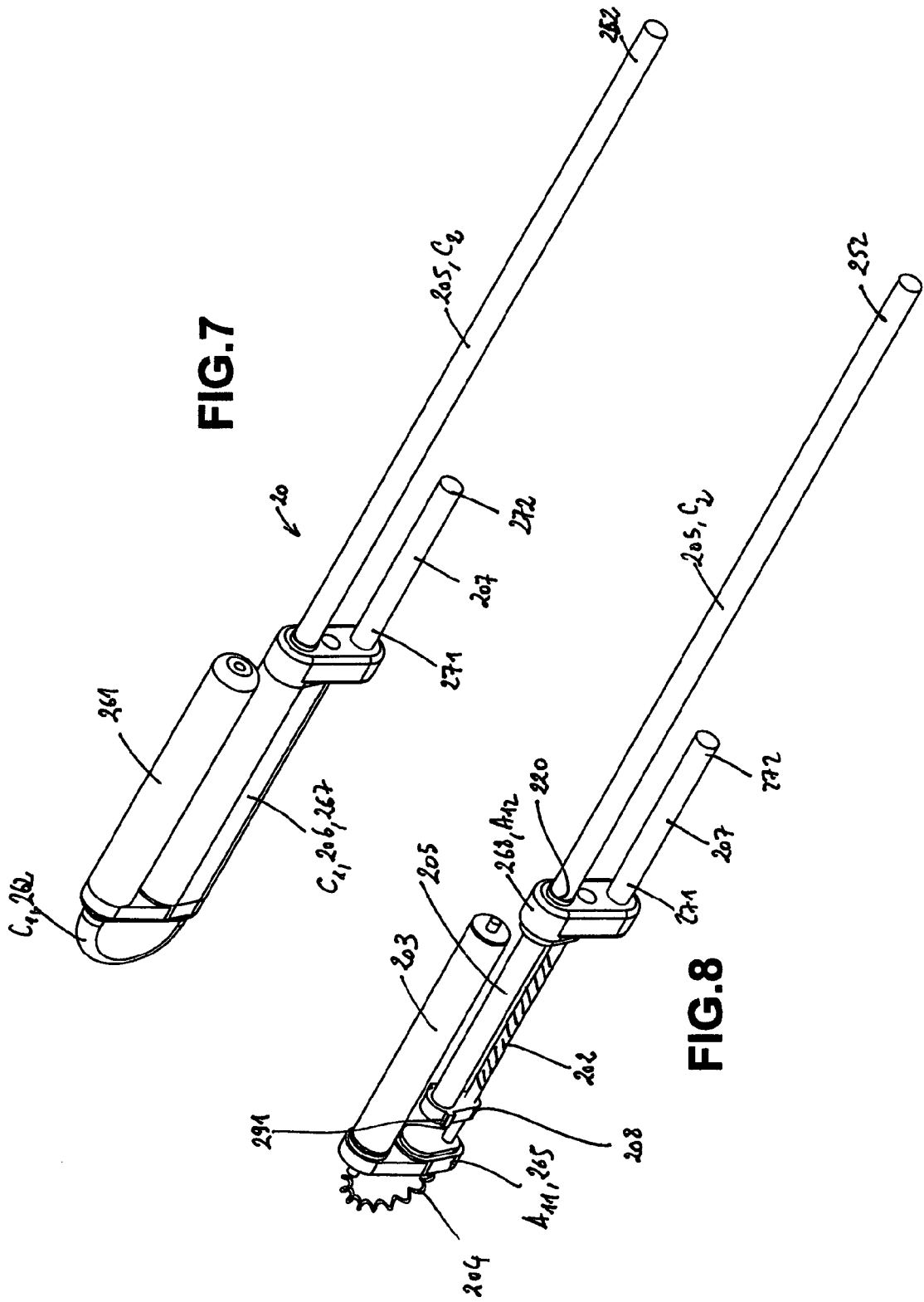

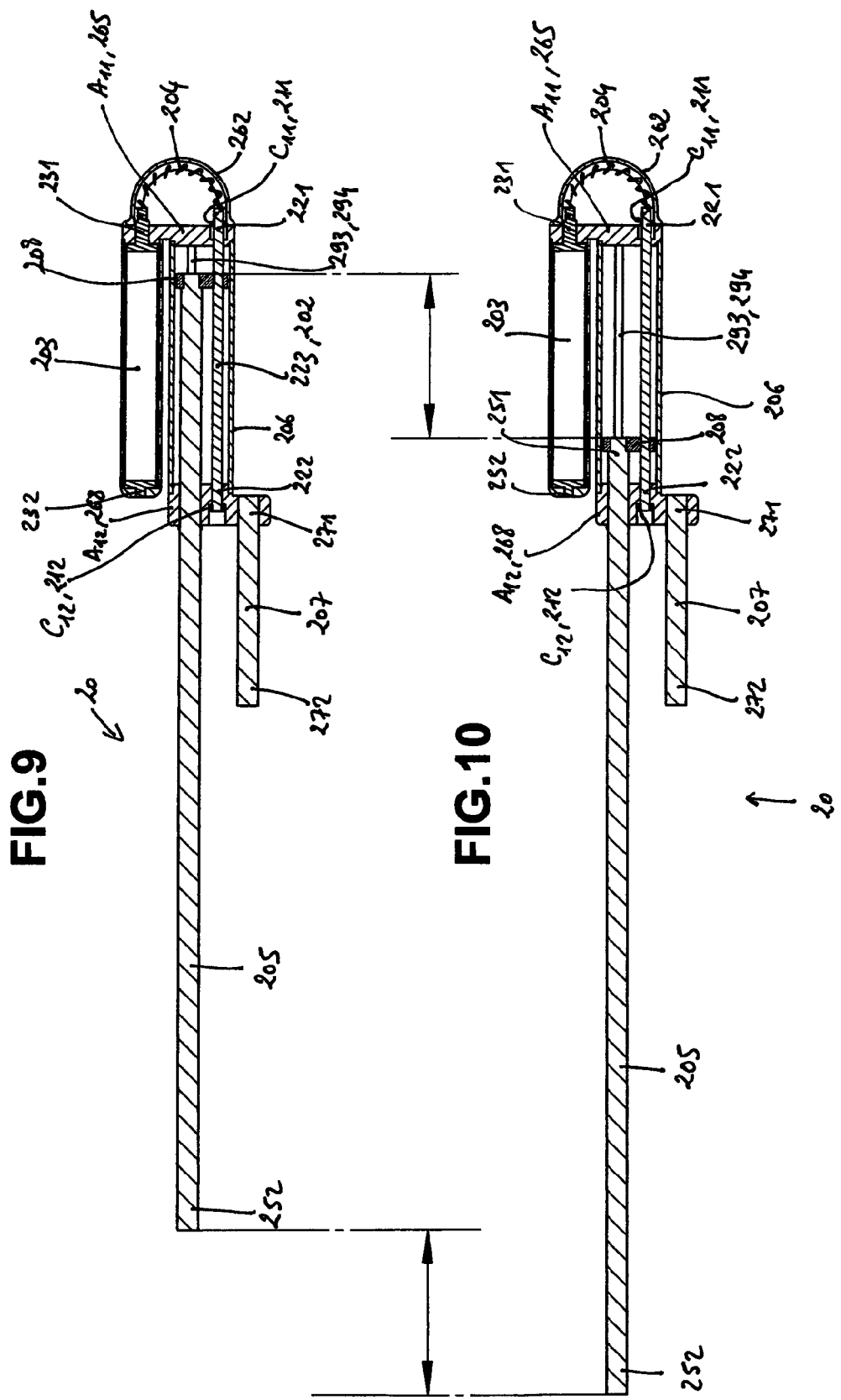

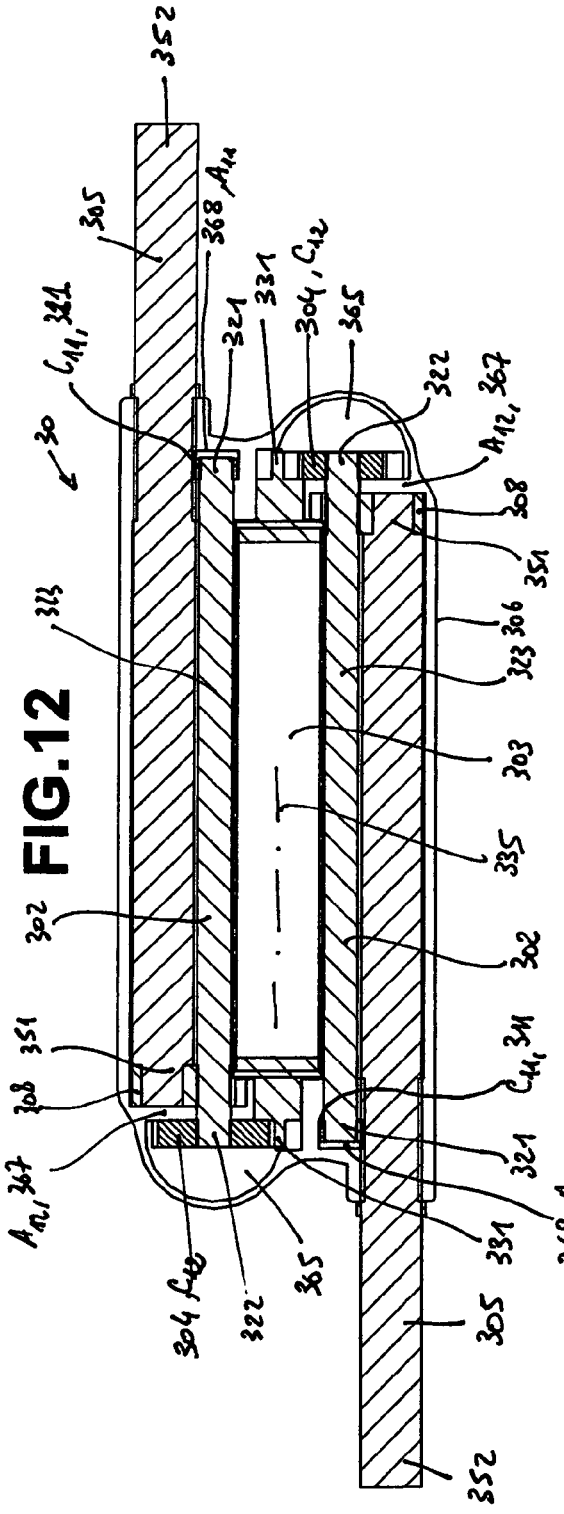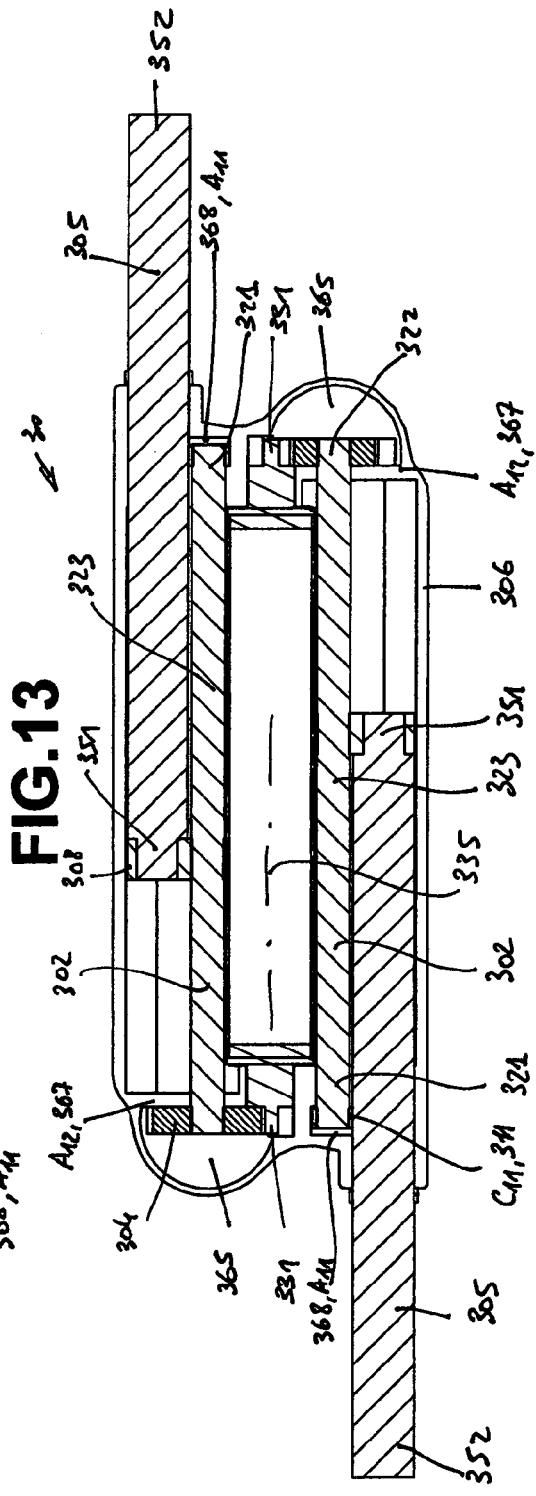

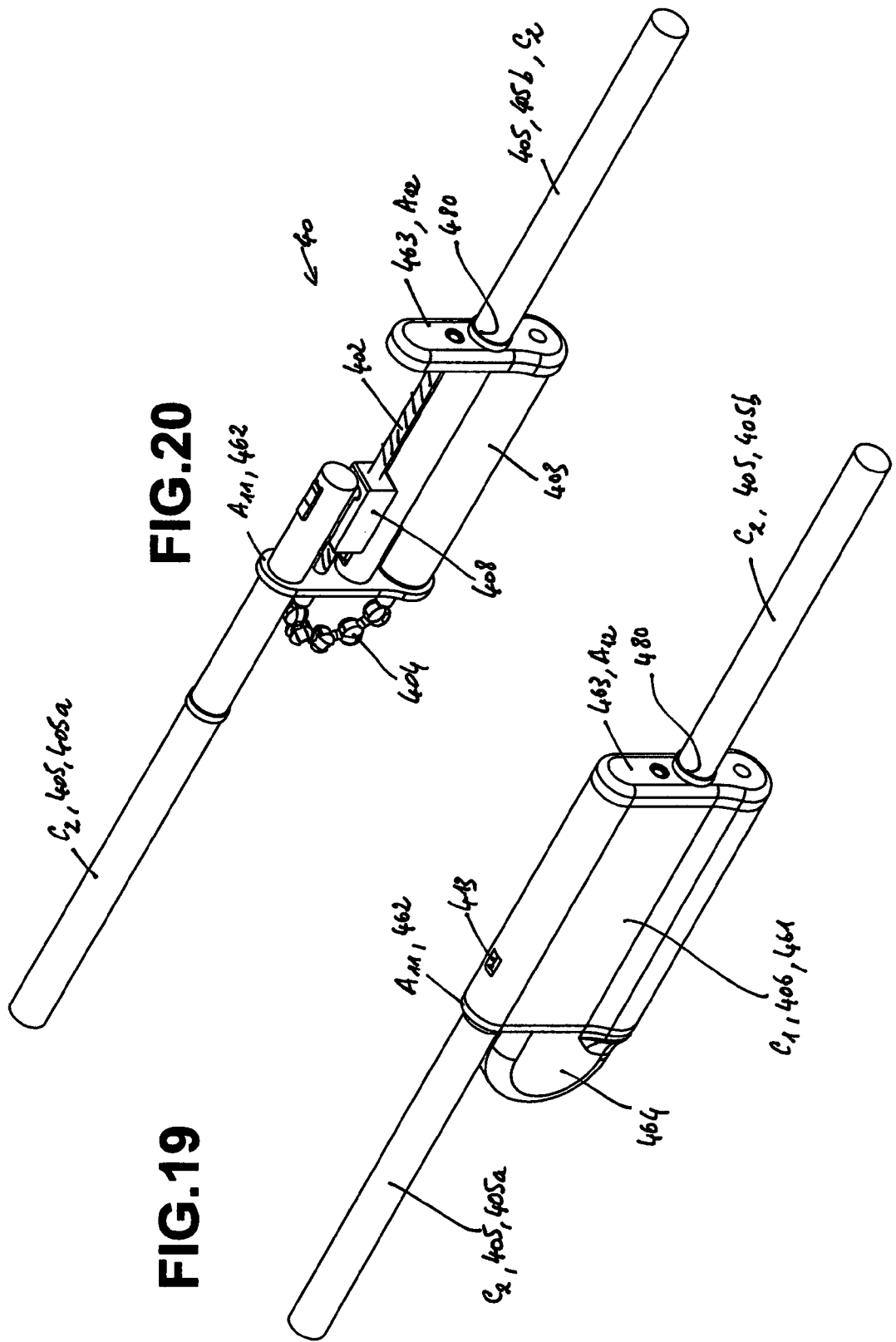

INTRACORPOREAL DEVICE FOR MOVING TISSUE

CROSS-REFERENCE TO RELATED APPLICATION

This is the national stage of International application Ser. No. PCT/FR2010/000608, filed Sep. 7, 2010, which claims the benefit of French application Ser. No. 0904306, filed Sep. 9, 2009.

TECHNICAL FIELD

The invention relates to a device for moving tissue in the human or animal body.

The invention more particularly, but not exclusively, relates to devices allowing the moving of bone portions.

The invention is particularly advantageously applicable in the following technical sectors:
 distraction or compression rods to correct the spine or the thorax by bearing on the vertebrae, ribs and/or pelvis;
 intramedullary nail or plate for bone lengthening or bone transport for long bones, flat bones, the jaw, or the skull;
 growth prostheses.

BACKGROUND OF THE INVENTION

Bone lengthening through progressive distraction of the callus that forms naturally when a bone is fractured before it calcifies was initially done using external fixators, for example as made popular by Ilizarov.

To try to correct the drawbacks of external fixators, such as infections or annoyances in daily life, completely implanted lengthening nails were proposed: Albizzia nails, through which the lengthening is caused by a deliberate rotation of the patient's leg, Bliskunov nails, Baumgart and Betz nails, or the ISKD (Intramedullary Skeletal Kinetic Distractor) nail by Cole.

The speed of lengthening of the bone, on the order of one millimeter per day, is adjusted according to clinical observations.

Bone transport allows for reconstructing, for example, part of the diaphysis of a bone removed following a trauma, an infection, or a tumor, by gradually stretching the callus that forms between a preserved bone portion and a bone slice that has been detached from that portion through osteotomy, until the slice abuts against the second preserved bone portion.

Documents WO 02/071962 and WO 95/24870 present examples of bone transport nails. These two devices operate through pawl systems, which are bulky, comprise a large number of parts, and are difficult to miniaturize. The movements necessary to elongate them are frequently painful.

Distraction using intracorporeal means for the surgical treatment of deformities of the spine have also been proposed, in particular to treat progressive scoliosis in children. A functional presentation of the surgical treatment instrumentations for deformities of the spine is provided by Foster et al (*The Spine Journal*, pp. 652-694, 2005).

In children, it is necessary not only to correct the deformity as well as possible, but also to maintain the obtained correction all throughout growth while limiting that growth as little as possible. This requires that the geometry of the implanted distractor evolve over time. To that end, most known distractors require repeated surgeries, with the associated difficulties, costs, and risks, in particular those of infection. This is the case of the devices described in documents WO 2006/010844, WO 2007/051924, FR 2900563, FR 2843538, FR 2891727, FR 2794357 and FR 2892617. This is also the case for the VEPTR® (Vertical Expandable Prosthetic Titanium Rib). In order to try to limit the number of surgical operations, several intracorporeal devices that may be elongated without reoperation have been proposed. For example, the vertebral distractor described in documents WO 01/78614 comprises a magnet steering the rotation of the wheel meshing with two diametrically opposite wheels and each provided with a tapping complementary to the thread of two elongation rods.

The use of gears and threads on the elongation rods necessitates that the device be sealed against the surrounding biological materials, which is technically very delicate and limits sterilization possibilities. Furthermore, the presence of a thread on the elongation rods, which are very stressed in fatigue, limits the lifetime of the implant or requires that it be overdimensioned, which then makes it too voluminous to be reasonably implanted in a child.

Document WO 2007/144489, in the applicant's name, describes an intracorporeal elongation device which may be used as a bone lengthening nail, bone transport nail, spine distraction rod, or growth prosthesis. The device described in document WO 2007/144489 comprises:
 a first elongated part,
 a second part telescopically mounted relative to the first portion,
 first means for connecting to the body, for example by screwing, at a first end of the first part,
 second means for connecting to the body, for example by screwing, at a first end of the second part,
 a rod comprising at least one thread whereof the rotation drives the movement of the second part relative to the first part,
 means for controlling the rotation of the rod, for example a permanent magnet, said rod being mounted between two ends that come closer together when the device elongates.

In the preferred embodiment described in this prior document by the applicant, the rod comprises, at a first end portion, a housing for a permanent magnet. A support tab is secured, for example by welding, to the second end portion of the rod. The support tab is secured to the first tubular part of the device, for example by welding, and is guided in longitudinal sliding relative to the second part of the device. Between the housing of the permanent magnet and the support tab, the threaded rod is screwed into a tapping of the second part of the device. A loaded rod length is thus defined between the tapping of the second part and the support tab rigidly connected to the first part of the device.

This prior device has many advantages. In particular, it is easy and inexpensive to manufacture in light of the function performed, has sufficient power for its function in a reduced volume, does not require particular sealing, can be controlled manually and painlessly using a simple external permanent magnet, in particular at home, by the patient or a layperson assisting the patient. Furthermore, the length of the loaded rod decreases when the device elongates, and the loaded rod length works in traction when the device elongates, which prevents any possibility of buckling.

The device described in document WO 2007/144489 does, however, have, for the desired power and elongation potential, a rigid straight length that makes it impossible to place in a location that is completely curved (such as applications to the spine and the thorax, for example) or a location where space is lacking lengthwise in the direction of movement that one wishes to gradually perform (such as for significant bone transports or elongations, or those of the jaw, for example). Furthermore, this device is capable of exerting a distraction or compression, but not both interchangeably, because it disassembles if a force is applied in the direction opposite that of the force it is capable of producing. The invention in particular aims to do away with these limitations while preserving the advantages of the device described in document WO 2007/144489 by proposing a new intracorporeal screw elongation device, with an adjustable length, in particular but not exclusively for an application to spine distraction or compression or bone transport.

BRIEF DESCRIPTION OF THE INVENTION

To this end, the invention relates, according to a first aspect, to a device for moving tissue inside the body, in particular bone tissue, said device including a first part referred to as a reference part; a second part, referred to as a transport part, which is slidably mounted relative to the reference part; a rod comprising at least one thread, referred to as the threaded rod, pivotably mounted relative to the reference part; a control shaft; driving means connecting the control shaft to the threaded rod; connecting means, referred to as the connecting nut, between the transport part and the threaded rod, said connecting nut being mounted onto the threaded rod and being rotatably guided relative to the reference part; and means for converting the movement of the connecting nut along the threaded rod into a movement of the transport part relative to the reference part, said device comprising, in order to limit the longitudinal translation of said threaded rod relative to the reference part, a first abutment and a second abutment rigidly connected to the threaded rod, these abutments respectively cooperating with a first bearing and a second bearing rigidly connected to the reference part, these bearings being placed at a distance from one another between said abutments, the connecting nut being movable along the threaded rod between the first bearing and second bearing.

The distance between the two abutments is advantageously larger than that between the bearings, so as to allow translational play of the threaded rod relative to the reference part.

In normal operation, the control shaft is rotated using any means known by those skilled in the art. For example, the control shaft can be associated with the permanent magnet which, when subjected to a magnetic field, pivots to orient itself in the field and drives the control shaft. Alternatively, the control shaft is connected to a motor, a gear motor, or a key gear.

The device has, according to various embodiments, the following features, which may be combined.

The driving means comprise a flexible transmission shaft and/or at least one helical spring and/or a transmission joint, a chain of transmission joints, a Cardan joint, or a chain of Cardan joints.

The driving means comprise an intermittent device, in particular a Geneva wheel mechanism, rigidly connected to the threaded rod and moved by the control shaft, said intermittent device being capable of converting a continuous rotational movement of the control shaft into an intermittent movement of threaded rod.

The conversion means comprise a pawl or a rigid connection between the connecting nut and the transport part or a bearing rigidly connected to the connecting nut, said bearing cooperating with an abutment rigidly connected to the transport part.

The rotational guiding of the connecting nut relative to the reference part may be a linear guiding or a helical guiding such that said connecting nut rotates by an angle comprised between 10 and 180° when it moves from said first to said second bearing, or vice versa.

Advantageously, the device comprises two transport parts and two threaded rods. Advantageously, the threads of the two threaded rods have different diameter, direction, or pitch characteristics. Each threaded rod is advantageously provided with an intermittent device moved by a control shaft, each intermittent device being able to convert a continuous rotational movement of the control shaft into an intermittent movement of each threaded rod, the two intermittent devices being mounted in opposition, such that when one of the devices is in the driving state, the other is in the blocking state.

The diameter of the threaded rod(s) is smaller than four mm, in particular comprised between one and three millimeters.

When the device comprises two transport parts, they are advantageously driven by a shared control shaft. The transport parts may or may not be substantially parallel to one another.

Advantageously, the transport parts are substantially cylindrical and have a normal diameter in vertebral surgery, in particular comprised between three and seven millimeters.

In certain embodiments, the transport parts are provided with a portion substantially in the form of plates comprising normal screw passage openings in orthopedics for long bones or in maxillofacial surgery.

Advantageously, the control shaft comprises a permanent magnet whereof the direction of magnetization is substantially perpendicular to the axis of rotation of the control shaft. The control shaft in particular comprises a rare earth-based permanent magnet, more particularly Neodymium Iron Boron.

The control shaft can be connected to a motor, a gear motor, or a key gear. Advantageously, the control shaft comprises a hollow cylinder in which a magnet is secured using a silicone-based adhesive.

Advantageously, the device is at least partially made using an electrochemical manufacturing technique, in particular the EFAB Technik.

Advantageously, the reference part comprises a sheath in which a bone transport carriage slides on which a transport part is mounted. The bone transport carriage is provided with a through tapped longitudinal piercing, at a distance from the axis of the sheath, said piercing being complementary to the threading of the threaded rod. The bone transport carriage is provided with a diametric piercing housing a bone screw forming the transport part, said bone screw being slidably mounted in two longitudinal parallel grooves of the sheath.

In certain embodiments, the device comprises two transport parts slidably mounted in opposite directions relative to the reference part. Advantageously, the device comprises a single threaded rod, the conversion means being capable of transmitting a movement from the connecting nut in a first direction of movement, by sliding a first transport part relative to the reference part as far as an end position, the device comprising means for locking the first transport part in said end position. The conversion means are capable of transmitting a movement of the connecting nut in a second direction of movement opposite the first direction, by sliding a first transport part relative to the reference part. Advantageously, the conversion and locking means comprise a pawl system.

The invention is applicable as lengthening or bone transport intramedullary nail or plate in particular for long bones, flat bones, and those of the jaw or skull.

The invention is also applicable as distraction or compression rod to correct the spine or the thorax, or as a growth prosthesis.

The invention is also applicable to the modification of soft tissue, in particular the elongation of part of the intestine or gastric bands, or to modify sections of the conduits of the blood system, in particular artery banding, valvuloplasty rings.

BRIEF DESCRIPTION OF THE DRAWINGS

Other objects and advantages of the invention will appear in light of the following description provided in reference to the appended drawings, in which:

FIG. 2 is a perspective view of the assembled device of FIG. 1;

FIG. 3 is a view similar to that of FIG. 2 in which the inside of the device is visible;

FIG. 4 is a cross-sectional view of the device of FIG. 2 in a first position;

FIG. 5 is a cross-sectional view of the device of FIG. 2 in a second position;

FIG. 7 is a perspective view of the assembled device of FIG. 6;

FIG. 8 is a view similar to that of FIG. 7 in which the inside of the device is visible;

FIG. 9 is a cross-sectional view of the device of FIG. 6 in a first position;

FIG. 10 is a cross-sectional view of the device of FIG. 6 in a second position;

FIG. 12 is a cross-sectional view of the device of FIG. 11 in a first position;

FIG. 13 is a cross-sectional view of the device of FIG. 11 a second position;

FIG. 19 is a perspective view of a tissue movement device according to a fourth embodiment;

FIG. 20 is a view similar to FIG. 19 in which the inside of the device is visible;

DETAILED DESCRIPTION OF THE INVENTION

Figure 1:
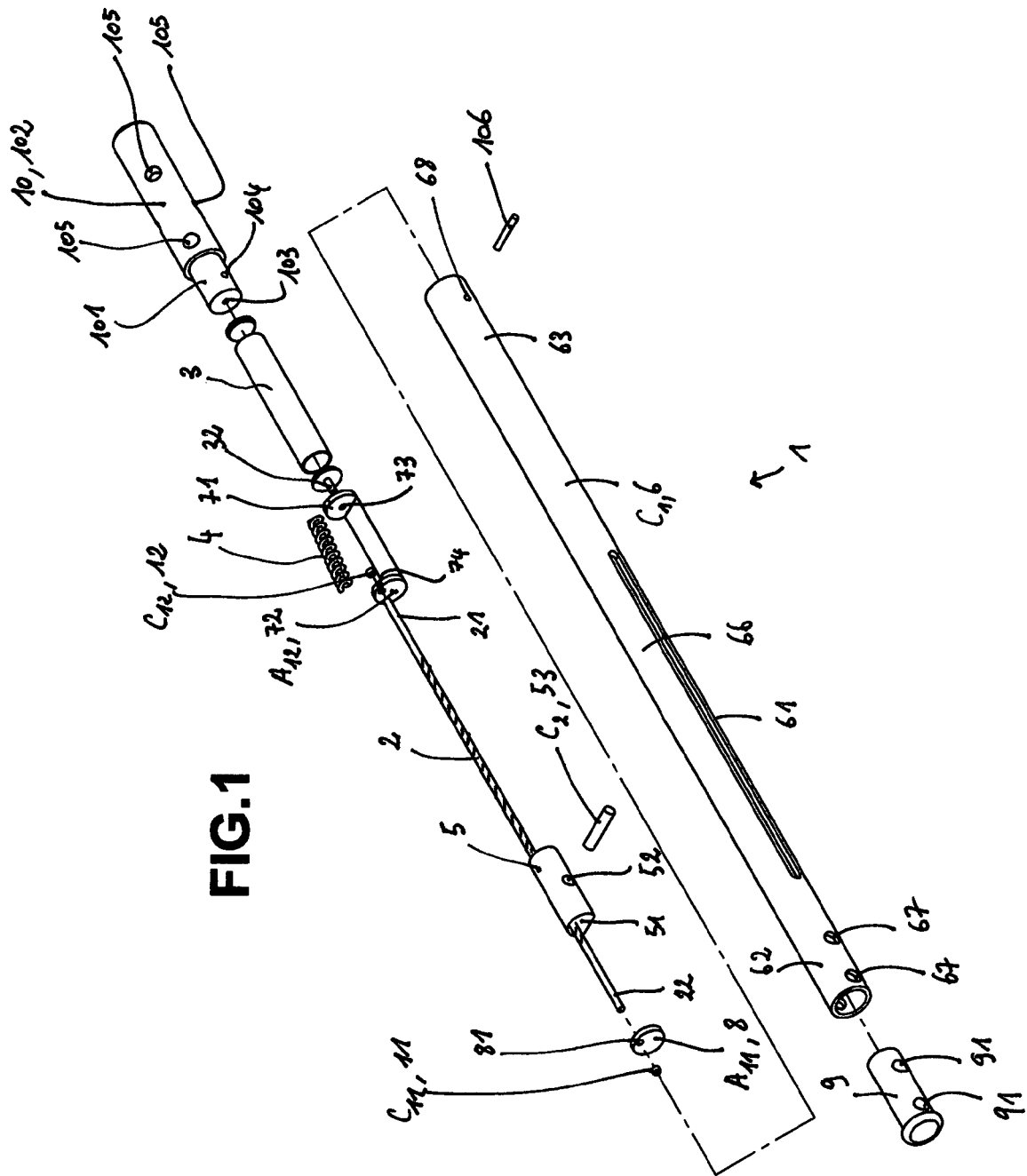
FIG. 1 is an exploded perspective view of a tissue displacement device according to a first embodiment.
Figure 6:
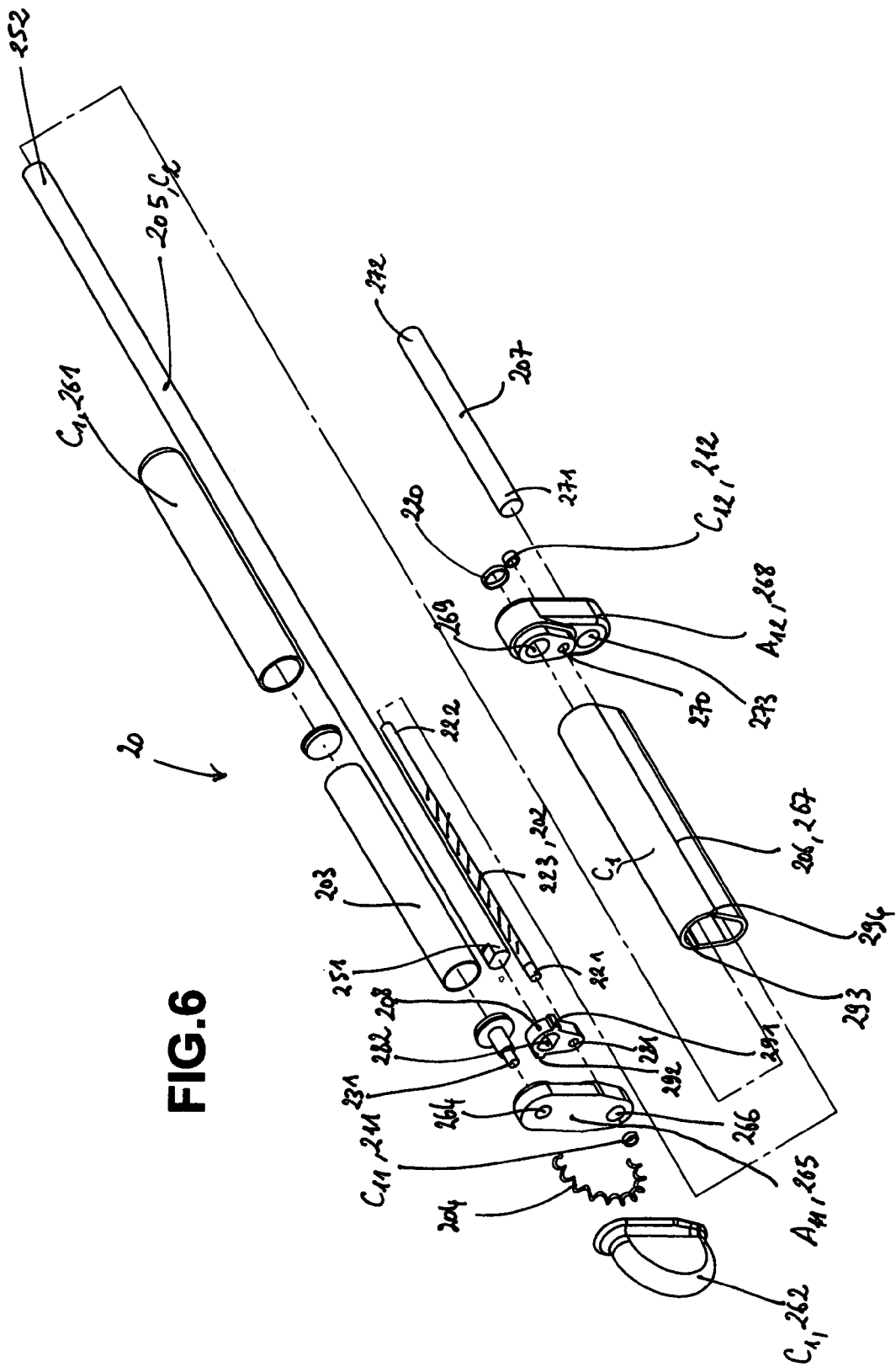
FIG. 6 is an exploded perspective view of a tissue movement device according to a second embodiment.

We will now refer to FIGS. 1 to 5, which illustrate a first embodiment, well-suited to bone transport or lengthening.

The bone transport nail 1 comprises a threaded rod 2, a control shaft 3, a flexible transmission shaft 4 between the threaded rod 2 and the control shaft 3. The first part $C_1$, referred to as the reference part, comprises a sheath 6, in which a bone transport carriage 5 slides.

The threaded rod 2 comprises two end portions 21, 22 on either side of a threaded portion 23, one end portion 21 being smooth.

The control shaft 3 assumes the form of a hollow cylinder, in which a magnet is secured, for example using a silicone-based adhesive. At each of its ends, the control shaft 3 comprises an axial lug 31, 32.

The flexible transmission shaft 4 is placed between the edges of a part 7 in the form of a U-shaped stirrup whereof the opposite flanges 71, 72 are longitudinally pierced. The piercing 73 of a first flange 71 of the stirrup 7 houses an axial lug 32 of the control shaft 3. The piercing 74 of the second flange 72 of the stirrup 7 is parallel to and at a distance from the axis of the sheath 6 and houses the smooth end portion 21 of the rod 2.

In one embodiment, the flexible transmission shaft 4 is of the type marketed by the company SUHNER. The flexible transmission shaft assumes the form of one or more helical springs wound around a same central axis. A flexible sheath can surround the flexible shaft to protect it.

In FIGS. 1 to 5, a single spring is shown. However, the flexible transmission shaft 4 can be made up of several layers of helical springs wound around one another, each layer being able to comprise several juxtaposed identical springs. Preferably, the coils of the springs of a same layer are not touching, so as to limit deformation and friction creating losses, and to allow a small curve radius of the flexible shaft. Advantageously, the pitch of the springs is just larger than or equal to the smallest desired inner radius of the flexible transmission multiplied by $\pi$ and divided by the number of springs on the considered layer and the diameter of the wire making up said springs.

The transport carriage 5 assumes the form of a cylinder truncated by a longitudinal plane. The carriage 5 is provided with a through tapped longitudinal piercing, at a distance from the axis of the sheath 6, said piercing 51 being complementary to the thread of the threaded portion 23 of the rod 2.

The carriage 5 is provided with a diametric piercing 52 housing a bone screw 53.

The sheath 6 assumes the form of a hollow cylindrical part, provided with two longitudinal parallel grooves 61, placed opposite one another in which the bone screw 53 slides.

The carriage 5 forms connecting means, referred to as a connecting nut, between the transport part $C_2$ (bone screw 53) and the threaded rod 2, the carriage 5 being mounted on the threaded rod 2 and guided in rotation relative to the sheath 6 belonging to the reference part $C_1$.

The means for converting the movement of the connecting nut (the carriage 5) into a movement of the transport part (bone screw 53) are formed by the rigid connection between the connecting nut and the transport part.

The axis of rotation of the rod 2 is defined by the piercing 74 of the second flange 72 of the stirrup 7 and by a piercing 81 of a bearing shim 8.

The sheath 6, closed at a distal end 62 by a distal fastening part 9 in the form of a plug and a proximal end 63 by a proximal fastening part 10, forms a housing for all of the mobile elements of the bone transport nail 1.

From its distal end 62, the sheath 6 has a distal inner region 64 with a section complementary to that of the bearing shim 8.

From its proximal end 63, the sheath 6 has a proximal inner region 65 with a section complementary to that of the flanges 71, 72 of the stirrup 7.

In an intermediate inner region 66, the inside of the sheath 6 has a substantially circular section, with a diameter smaller than that of the bearing shim 8 and the flanges 71, 72 of the stirrup 7, so that the inside of the sheath 6 forms two abutments, respectively between the distal region 64 and the intermediate region 66, and between the intermediate region 66 and the proximal region 65.

On its distal end portion 62, the sheath 6 comprises two distal diametric piercings 67, and on its proximal end portion 63, the sheath 6 comprises a proximal diametric piercing 68.

The distal fastening part 9 assumes the form of a cylindrical plug with a diameter substantially equal to that of the section of the distal inner region 64 of the sheath 6. This distal fastening part 9 is provided with two diametric piercings 91.

The proximal fastening part 10 comprises two portions 101, 102. The first portion 101 of the proximal fastening part 10 is cylindrical, with a diameter substantially equal to that of the section of the proximal inner region 65 of the sheath 6, and comprises a longitudinal piercing 103 and a diametric piercing 104.

The second portion 102 of the proximal fastening part 10 is cylindrical, with a diameter larger than that of the first portion 101, and is provided with three diametric piercings 105, longitudinally distributed and angularly offset by 90°, and capable of receiving bone screws.

The assembly of the nail 1 can be obtained as follows.

The threaded rod 2 is inserted into the tapped longitudinal piercing 51 of the bone transport carriage 5. The smooth end portion 21 of the rod 2 is also inserted into the piercing 74 of the flange 72 of the stirrup 7. In this way, the axis of rotation of the threaded rod 2 is at a distance from the axis of symmetry of the bone transport carriage 5.

A second nut 12 forming a second axial abutment $C_{12}$ is screwed and blocked in rotation, for example by laser welding, on the end portion 21 of the rod 2, and is placed against the second flange 72.

The flange 72 forms a second bearing $A_{12}$, rigidly connected to the reference part $C_1$ so that the rod 2 is blocked in longitudinal translation in a first direction, while remaining free in rotation.

A lug 32 at one end of the control shaft 3 is pivotably mounted in the piercing 73 of the first flange 71 of the stirrup 7.

The flexible shaft 4 is then mounted between the two flanges 71, 72 of the stirrup 7, the end of the shaft 4 being welded respectively to the smooth end portion 21 of the threaded rod 2 and the lug 32 of the control shaft 3.

The bearing shim 8 is then inserted into the distal end 62 of the sheath 6, until it abuts at the boundary of the intermediate inner region 66.

The assembly formed, i.e. the threaded rod 2, the transport carriage 5, the stirrup 7, the transmission shaft 4, and the control shaft 3, is then inserted into the sheath 6, the second end 22 of the threaded rod 2 being inserted into the piercing 81 of the bearing shim 8. The stirrup 7 is placed as far as the bottom of the proximal inner region 65 of the sheath 6, while the threaded portion 23 of the rod 2 and the carriage 5 are placed in the intermediate inner region 66 of the sheath 6.

A first nut 11 forming a first axial abutment $C_{11}$ is screwed and welded, for example by laser, on the second end 22 of the threaded rod 2, against the shim 8.

The shim 8 forms a first bearing $A_{11}$, rigidly connected to the reference part $C_1$, and the rod 2 is thus blocked in longitudinal translation in a second direction, while remaining free in rotation.

The arrangement of the bearings $A_{11}$, 8 and $A_{12}$, 72, placed between the abutments $C_{11}$, 11 and $C_{12}$, 12, makes it possible for the threaded rod 2 only to be stressed in traction.

Then, both ends of the sheath 6 are closed by the fastening parts 9, 10.

To that end, the plug 9 is inserted into the distal inner region 64 of the sheath 6, so that its two diametric piercings 91 are aligned with the distal piercings 67 of the sheath 6 and can receive bone screws. The first cylindrical portion 101 of the proximal fastening part 10 is inserted into the proximal inner region 65 of the sheath 6, the second lug 31 of the control sheath 3 being inserted into the longitudinal piercing 103 of the proximal fastening part 10. Then, the proximal piercing 68 of the sheath 6 is aligned with the diametric piercing 104 of the first cylindrical portion 101. A lug 106 ensures the blocking of the proximal fastening part 10 relative to the sheath 6. Laser welds reinforce these assemblies.

In this way, the sheath 6 and the fastening parts 9, 10 make up a first part $C_1$, referred to as a reference part, the bone screw 53 forming a second part $C_2$, referred to as a transport part, the abutments $C_{11}$ and $C_{12}$ of the threaded rod 2 correspond to the axial abutment nuts 11, 12 placed against the bearing shim $A_{11}$, 8 and against the second flange $A_{12}$, 72 of the stirrup 7. The connecting nut is formed by the carriage 5 and the transmission of the movement of that carriage 5 to the transport part is obtained by the rigid connection between the connecting nut and the transport part.

An example of the operation of the bone nail 1 is provided below.

A bone, for example following the ablation of a tumor, comprises a missing portion between two healthy end portions. A first healthy portion undergoes an osteotomy, so as to free a slice between the two healthy end portions. The two portions and the slice are bored, so as to allow the passage of the nail 1.

The bone transport nail 1 is in an initial position, for example such that the transport carriage 5 is closer to the stirrup 7 than the bearing shim $A_{11}$, 8, the stretching of the bone callus being done from the stirrup 7 toward the bearing shim $A_{11}$, 8. Furthermore, the carriage 5 is advantageously positioned so that its diametric piercing 52 is opposite the longitudinal grooves 61 of the sheath 6.

The proximal fastening part 10 is secured in the first bone end portion using three bone screws passed into the piercings 105 of the second cylindrical portion 102 of the part 10.

The distal portion of the nail is secured in the second bone end portion, using two bone screws passed into the distal piercings 67 of the sheath 6 and into the piercings 91 of the distal fastening part 9.

A bone screw 53 makes it possible to fasten the bone slice to the carriage 5 through the diametric piercing 52 of the carriage 5 and the grooves 61 of the sheath 6.

The control shaft 3 is then pivoted by unknown value. Its rotation is transmitted to the threaded rod 2 via a flexible shaft 4, causing the carriage 5 to move toward the bearing shim $A_{11}$, 8, the bone screw $C_2$, 53 secured to the bone slice sliding along the grooves 61 of the sheath 6 and ensuring the translational guiding of the transport carriage 5, so that the bone slice is gradually moved away from the first bone end portion.

By performing this operation regularly, the bone callus forming between the bone slice and the first bone end portion is stretched, until it fills in the missing bone portion.

Once the junction between the bone slice and the second bone end portion and the bone callus has become solid, the device 1 may be left in the bone or removed through a surgical operation.

The flexible transmission shaft 4 advantageously makes it possible to skew the tapping 51 of the transport carriage 5 relative to the rest of the bone nail 1, so that the bone screw $C_2$, 53 secured to the bone slice can be inserted along a diameter of the nail 1.

The flexible transmission shaft 4 also makes it possible to form a non-zero angle between the control shaft 3 and the threaded rod 2, so as to adapt the shape of the bone transport nail 1 to its use, for example in the case of fastening on the jaw for transport or elongation.

An elongation can be obtained by not fastening the distal portion of the nail, which in that case does not have a hole to do so.

A second embodiment is shown in FIGS. 6 to 10.

This embodiment is more particularly adapted to the production of distraction or compression rods that can be connected to vertebrae, ribs, or the pelvis, to correct the spine or the thorax. That is why, in the rest of this description, reference will essentially be made to that application.

The distraction rod 20 comprises a threaded rod 202, a control shaft 203, a flexible transmission shaft 204 between the threaded rod 202 and the control shaft 203, a mobile rod 205, and a housing 206 housing the threaded rod 202 and the shafts 203, 204.

The housing 206 forms a first part $C_1$, referred to as a reference part. A fixed rod 207 is mounted on the housing 206. The mobile rod 205 forms a second part $C_2$, referred to as a transport part.

The threaded rod 202 and the control shaft 203 are not coaxial. In the illustrated embodiment, the axis of rotation of the threaded rod 202 is substantially parallel to the axis of rotation of the control shaft 203. The mobile rod 205 is mounted slidingly, inside the housing 206, the sliding axis of the mobile rod 205 being positioned substantially in the plane containing the axes of rotation of the threaded rod 202 and the control shaft 203.

In the illustrated embodiment, the sliding axis of the mobile rod 205 extends between the axes of rotation of the threaded rod 202 and the control shaft 203.

The control shaft 203 assumes the form of a hollow cylinder, in which a magnet is secured, for example using a silicone-based adhesive. The control shaft 203 comprises, at each of its ends, in alignment, a lug 231, 232 placed in the axis of the shaft 203.

The mobile rod 205 comprises a proximal end portion 251 and a distal end portion 252. The terms "distal" and "proximal" are used here in reference to the housing $C_1$, 206.

The distal end portion 252 of the mobile rod 205 is capable of receiving connecting means (not shown), such as hooks, screws, or tapes, for connecting to the bones (in particular vertebrae, ribs, or pelvis) to which one wishes to attach it.

The fixed rod 207 comprises a proximal end portion 271 and a distal end portion 272. The proximal end portion 271 of the fixed rod 207 is embedded in the housing $C_1$, 206. The distal end portion 272 of the fixed rod 207 is capable of receiving connecting means (not shown), such as hooks, screws, or tapes, for connecting to the bones (in particular vertebrae, ribs, or pelvis, to which one wishes to attach it.

In the illustrated embodiment, the mobile rod 205 and the fixed rod 207 are substantially straight and parallel, and can be cut and curved by the surgeon. In other embodiments, not shown, at least one of these two elements 205, 207 is provided arched.

The threaded rod 202 is provided with two smooth end portions 221, 222 on either side of the threaded portion 223.

A lens 208 forms connecting means between the transport part $C_2$, 205 and the threaded rod 202. This lens 208, or connecting nut, comprises a tapping 281 complementary to the threaded portion 223 of the rod 202. The proximal end 251 of the mobile rod 205 is shaped to be inserted, for example by force, into a complementary opening 282 of the lens 208. Protuberances 291, 292 rigidly connected to said lens 208 and substantially symmetrical relative to the opening 282 respectively cooperate with grooves 293, 294 formed inside the housing $C_1$, 206 to ensure the rotational guiding of the connecting nut 208 relative to the reference part $C_1$.

When, in addition to distraction or compression, one wishes to produce torsion, said protuberances 291, 292 and said grooves 293, 294 can advantageously be helical, forcing the gradual rotation of the mobile rod 205 as it moves relative to the housing $C_1$, 206, and thus that portion of the treated spine portion. Similarly, a helical guiding of the connecting nut is of interest when, in addition to elongating a bone, one wishes to correct a torsional deformation of that bone at the same time.

The flexible transmission shaft 204 connects a first lug 231 of the control shaft 203 to the smooth end 221 of the threaded rod 202.

The housing $C_1$, 206 comprises a cylindrical sheath 261 in which the control shaft 203 is housed, the second lug 232 of the control shaft 303 being inserted into a recess of the sheath 261.

The first lug 231 of the control shaft 203 passes through a first opening 264 of the support part 265, secured to the cylindrical sheath 261 for example by interlocking and welding.

A first end 221 of the threaded rod 202 is inserted into a second opening 266 of the support part 265, so that it emerges on a same side as the first lug 231 of the control shaft 203. The threaded portion 223 of the rod 202 then extends at least partially from the opposite side of the support part 265.

A first nut 211 forms a first axial abutment $C_{11}$ of the threaded rod 202. This nut 211, $C_{11}$ is screwed and welded, for example by laser welding, on the first end 221 of the threaded rod 202 against the support part 265.

The support part 265 forms a first bearing $A_{11}$, rigidly connected to the reference part $C_1$, 206.

The flexible shaft 204 is secured, for example by welding, on the first lug 231 of the control shaft 203 and on the first end 221 of the threaded rod 202. The flexible shaft 204 than describes a curve, substantially in the shape of an arc of circle or a U.

The housing $C_1$, 206 also comprises a shell 262 forming a housing for the flexible transmission shaft 204. The shell 262 is in turn secured to the support part $A_{11}$, 265.

The lens 208 is inserted into the sheath 267 preferably with slight play. The lens 208 cooperates with the threaded rod 202 via the tapping 281, is secured on the mobile rod $C_2$, 205, and is guided in rotation via protuberances 291, 292 cooperating with the grooves 293, 294 of the sheath 267, part of the housing $C_1$.

The sheath 267 is assembled at one of its ends against the support part $A_{11}$, 265. The other end of the sheath 267 is closed by a cover 268 comprising a first opening 269 allowing the mobile rod 205 to pass.

The cover 268 also comprises a second opening 270 receiving the second end portion 222 of the threaded rod 202.

The cover 268 forms a second bearing $A_{12}$, rigidly connected to the reference part 206, $C_1$.

An axial blocking nut 212 forms a second stop $C_{12}$ and is inserted on the second end 222 of the threaded rod 202 against the cover 268, $A_{12}$.

The proximal end portion 271 of the fixed rod 207 is rigidly connected to the cover $A_{12}$, 268, for example by forcibly inserting it into a third opening 273 of the cover $A_{12}$, 268 and welding the end thereof.

The two sheaths 261, 267, the shell 262, the support part 265, and the cover $A_{12}$, 268 forming the housing $C_1$, 206 are for example assembled by laser welding or adhesion.

As appears in particular in FIGS. 7 to 10, the distraction rod 20 is generally J-shaped, the housing $C_1$, 206 forming the rigid and non-shapeable portion of the device advantageously being able to be placed above or below the area concerned by the surgical treatment.

The fixed rod 207 can also be secured to the cover 268 in the opposite direction to form an I-shaped rod 20 that is better adapted if it must be secured very high and very low on the spine.

The housing 206 forms a first part $C_1$, referred to as the reference part, the mobile rod 205 forms a transport part $C_2$, the abutments $C_{11}$ and $C_{12}$ of the threaded rod 202 are formed by the axial abutment nuts 211, 212 placed against the bearings $A_{11}$ and $A_{12}$ respectively formed by the support part 265 in the cover 268 of the housing $C_1$, 206.

The lens 208, or connecting nut, forms connecting means between the transport part $C_2$, 205 and the threaded rod 202. The means for converting the movement of the connecting nut 208 into a movement of the transport part $C_2$, 205 are formed by a rigid connection between the connecting nut 208 and the transport part $C_2$, 205, for example by forcibly inserting the end portion 251 of the transport part $C_2$, 205 into the opening 282 of the lens 208.

An example of the operation of the distractor 20 is provided below.

The distal end portion 252 of the mobile rod 205 is for example secured to a first vertebra, and the distal end portion 272 of the fixed rod 272 is secured to a second vertebra, for example situated below the first vertebra. The fastenings are done on the concave or convex side of a curve depending on the case, and depending on whether one wishes to apply a distraction or compression to the treated portion of the spine, respectively.

A magnetic field in which the magnet orients itself is applied: the pivoting magnet drives the control shaft 203. The pivoting of the control shaft 203 is transmitted to the threaded rod 202 via the flexible transmission shaft 204. The lens 208, helically connected with the threaded rod 202, moves along the threaded portion 223 of the rod 202, driving the mobile rod $C_2$, 205 in the direction of a distraction or a compression.

A viewing ring 220 is advantageously welded to the mobile rod $C_2$, 205 and makes it possible to easily view the movement performed on an x-ray.

The two vertebrae are thus gradually moved apart or closer together, causing a modification in the curvature of the spine.

Advantageously, the capacity of the rod 20 to evolve in both directions is used to periodically release the force applied on the spine so as to periodically and temporarily give it part of its mobility, and thereby delay the degeneration of the disks and the spontaneous fusion generally observed after several years of maintenance with the known fixed materials.

In the event the length variation of the rod 20 is accompanied by a rotation, the distal end portion 252 of the mobile rod 205 is secured to a vertebra, and the distal end portion 272 of the fixed rod 207 is secured to the pelvis if there is cause to correct a torsion of the spine relative to the pelvis.

In the most frequent case of scoliosis treatment, one advantageously combines, on the spine to be treated, two rods head to tail on either side of the apex of the curve whereof the distal end portion 252 of the mobile rod 205 is connected to said apex, and the distal end portion 272 of the fixed rod 207 is respectively secured, for one, to a vertebra with little or no rotation situated above the apex and, for the other, to a vertebra with little or no rotation situated below the apex. In this way, one simultaneously helps straighten and untwist the scoliosis.

In the illustrated embodiment, the control shaft 203 is connected to a single mobile rod 205.

In one alternative, not shown, the second lug 232 of the control shaft 203 is also secured to a second flexible transmission shaft transmitting the rotation of the control shaft to a second threaded rod, causing the movement of a second mobile rod $C_2$. In one embodiment, this second mobile rod slides in the direction of movement of the first mobile rod $C_2$, 205 and in the opposite direction. In another embodiment, this second mobile rod slides in a direction forming an angle with the direction of movement of the first mobile rod $C_2$, 205.

The flexible transmission shaft 204 thereby makes it possible to easily and economically produce J- or I-shaped rods that can be indifferently elongated or shortened at any time and whereof the portion that cannot be cut and curved by the surgeon has a length compatible with placement on the spine or the thorax.

According to another preferred embodiment, the driving means connecting the control shaft the threaded rod comprise an indexing device or an intermittent device.

This preferred embodiment will be presented in reference to FIGS. 11 to 18, in which a distraction or compression rod comprising two mobile rods is shown.

The distraction rod 30 comprises two threaded rods 302, a control shaft 303, an intermittent device 304 between each threaded rod 302 and the sole control shaft 303, two mobile rods 305, and the housing 306.

The threaded rods 302 and the control shaft 303 are not coaxial. In the illustrated embodiment, the axes of rotation of the threaded rods 302 are substantially parallel to the axis of rotation of the control shaft 303. The mobile rods 305 are slidingly mounted, inside the housing 306, the sliding axes of the mobile rods 305 being substantially positioned in the plane containing the axes of rotation of the threaded rods 302 and the control shaft 303.

In the illustrated embodiment, the axis of rotation of the control shaft 303 is positioned at an equal distance from the axes of rotation of the threaded rods 302.

The control shaft 303 assumes the form of a hollow cylinder, in which the magnet is secured, for example using a silicone-based adhesive. The control shaft 303 comprises two lugs 331, 332 at each of its ends.

A first lug 331 has a crescent-shaped section, placed substantially in the binding axis of the control shaft 303. The first lug 331 comprises a concave peripheral surface 333 and a convex peripheral surface 334. The concave surface 333 crosses the binding axis 335 of the control shaft 303, while the convex surface 334 is coaxial to the binding axis 335.

The second lug 332 extends substantially parallel to the binding axis 335 of the control shaft 303 and at a distance from said axis 335.

Each mobile rod 335 comprises a proximal end portion 351 and distal end portion 352. The terms "proximal" and "distal" are used here in reference to the housing 306.

The distal end portion 352 is capable of receiving connecting means (not shown), such as hooks, screws, or tapes, for connecting to the bones (in particular vertebrae, ribs, or pelvis) to which one wishes to attach it.

In the illustrated embodiment, the mobile rods 305 are substantially straight and parallel and can be cut and curved by the surgeon. In other embodiments not shown, at least one of these mobile rods 305 can be provided arched.

Each threaded rod 302 is provided with two smooth end portions 321, 322 on either side of the threaded portion 323.

Figure 11:
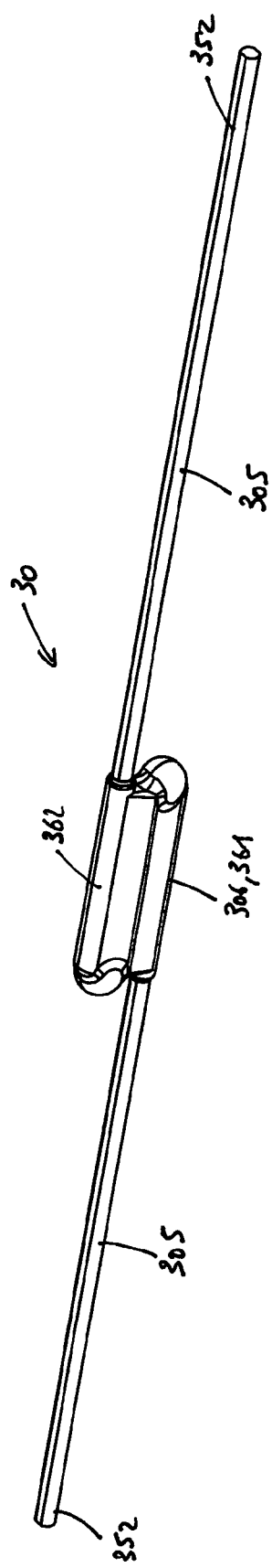
FIG. 11 is a perspective view of a tissue movement device according to a third embodiment.
Figure 14:
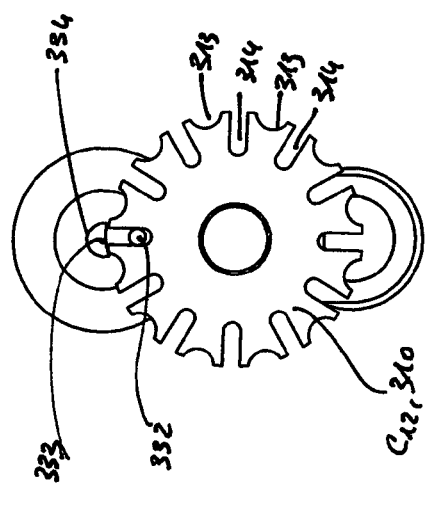
FIGS. 14 to 18 are front views of an intermittent device connected to a control shaft, in five different positions.
Figure 15:
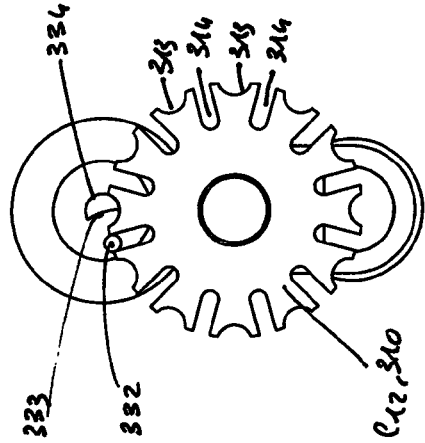
Figure 16:
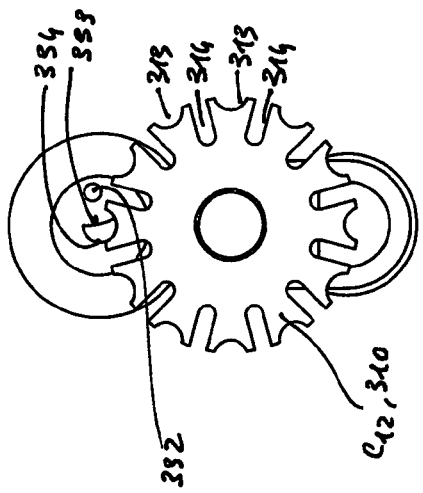
Figure 17:
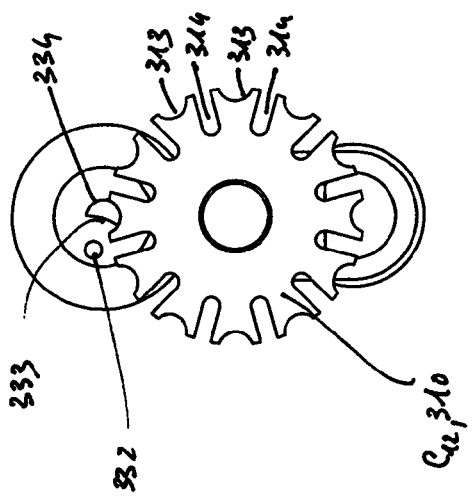
Figure 18:
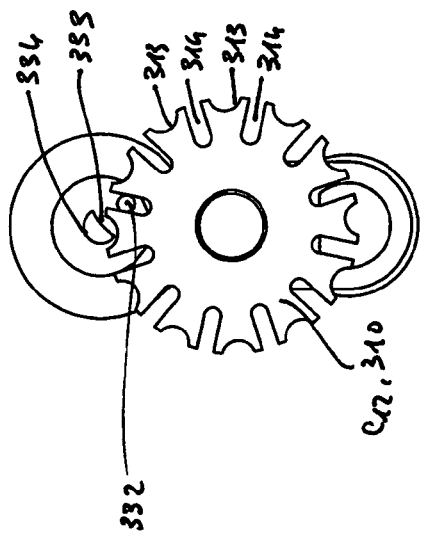
Figure 21:
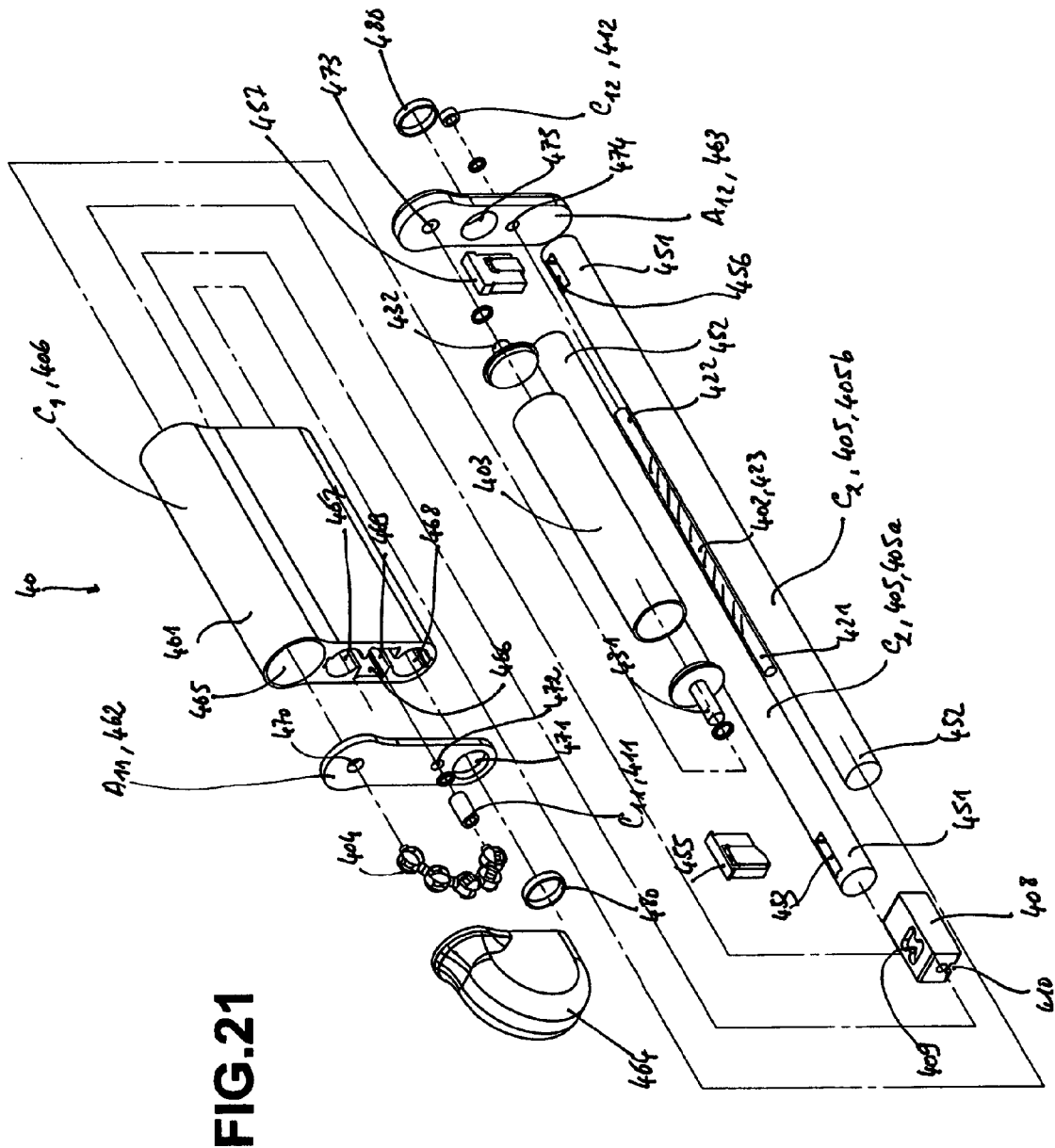
FIG. 21 is an exploded perspective view of the device shown in FIGS. 19 and 20.

As appears in FIGS. 11, 12 and 13, two mobile rods 305 extend substantially symmetrically on either side of the control shaft 303.

Each threaded rod 302 cooperates with a lens 308, provided with a complementary tapping of the threaded portion 323 of the rod 302. The proximal end 351 of each mobile rod 305 is shaped to be inserted, for example forcibly, into a complementary opening of a lens 308. Advantageously, the lenses 308 do not have any symmetry of revolution.

The illustrated housing $C_1$, 306 has a central symmetry and comprises two shells 361, 362, for example assembled by screwing. The housing 306 comprises two passage openings for the mobile rods 305.

The control shaft 303 is placed in a central accommodation of the housing 306, the lugs 331, 332 of each end emerging in an end accommodation 365.

The mounting of a threaded rod 302 and a mobile rod 305 with a lens 308 in the housing $C_1$, 306 is done as follows.

A first end 321 of the threaded rod 302 is inserted into an opening of the wall 367 in the housing 306 so as to emerge in an end accommodation 365. The threaded portion 323 of the rod 302 then extends at least partially on the opposite side of the wall 367. A longitudinal abutment, described later, is made between the first end portion 321 of the rod and the wall 367.

The second end part 322 of the threaded rod 302 is placed in a recess 368 of the housing 306.

A first nut 311 forms a first abutment $C_{11}$ in the recess 368 forming a bearing $A_{11}$ to longitudinally block the threaded rod 302.

The lens 308 cooperating with the threaded rod 302 via the tapping 381 and rigidly connected to the mobile rod 305 is inserted in sliding connection into an accommodation with a substantially complementary shape, and preferably leaving slight play. As in the previous embodiment of the invention, a helical connection can be used in place of the sliding connection to act on the curve and torsion of scoliosis at the same time by connecting each of the mobile rods 305 on either side of the apex of the curvature to vertebrae with little or no rotation and the housing $C_1$ at that apex.

When the rotation of the control shaft 303 is transmitted to the threaded rods 302, each lens 308 moves along a threaded rod 302, driving the mobile rod 305 rigidly connected to the lens 308.

In each end accommodation 365 of the housing 306, an intermittent device 304 is placed to transmit the rotation of the control shaft 303 to each rod 305.

Each intermittent device 304 comprises means so that, when the control shaft 303 performs a complete rotation, the threaded rod 302 with which it cooperates is only pivoted in one direction (clockwise or counterclockwise), the corresponding mobile rod 305 only having moved in a single direction.

Each intermittent device 304 can assume two states.

In a first state, referred to as a driving state, the intermittent device 304 transmits the rotation from the control shaft 303 to the threaded rod 302, to cause the mobile rod 305 to move.

In a second state, referred to as a blocking state, the intermittent device does not transmit the rotation from the control shaft 303 to the threaded rod 302, the mobile rod 305 remaining immobile in the housing 306.

Advantageously, each intermittent device 304 comprises a Geneva wheel mechanism 310, coaxial with the threaded rod 302 on which it is rigidly mounted, for example by forcibly inserting the first end portion 321 of the emerging threaded rod 302 into the end accommodation 365 in a central opening of the Geneva wheel mechanism 310.

The Geneva wheel mechanism 310 also forms an axial abutment $C_{12}$ against the wall 367 forming a bearing $A_{12}$, so that each threaded rod 302 is blocked in longitudinal translation by the nut $C_{11}$, 311 and the Geneva wheel mechanism $C_{12}$, 310 respectively bearing against the recess $A_{11}$, 368 and the wall $A_{12}$, 367.

The Geneva wheel mechanism 310 assumes the form of the toothed wheel, in which the teeth are formed by an alternation of two types of notches:

a short notch 313, in the shape of a half circle, with a radius substantially equal to that of the convex peripheral surface 334 of the crescent-shaped lug 331 of the control shaft 303;

a long notch 314, in the shape of a U, extending radially over a greater depth than the short notch 313, and with a width substantially equal to the diameter of the skewed lug 332 of the control shaft 303.

The operation of a Geneva wheel mechanism 310 in cooperation with the control shaft 303 is detailed here, in reference to FIGS. 14 to 18.

In a starting position, a crescent-shaped lug 331 on a first end of the control shaft 303 is positioned in a first short notch 313 of the wheel mechanism, the convex surface 334 being in contact with the bottom of the notch 313. The control shaft 303 pivots in the short notch 313 without driving the wheel mechanism 310: the intermittent device 304 is in the blocking position.

The control shaft 303 continuing to pivot, the skewed lug 332 on the first end of the control shaft 303 engages in the long notch 314 adjacent to the first short notch 313, while the convex peripheral surface 334 of the crescent-shaped lug 331 leaves the short notch 313 and the concave surface 333 comes opposite the bottom of the short notch 313, freeing the short notch 313. The skewed lug 332 then rotates the wheel mechanism 310: the intermittent device 304 is in the driving position.

The control shaft 303 continues to pivot, driving the wheel mechanism 310, the skewed lug 332 sliding along the long notch 314.

When the skewed lug 332 leaves the long notch 314, the convex peripheral surface 334 of the crescent-shaped lug 331 engages in the following short notch 313, again blocking the transmission.

In the illustrated embodiment, the two mobile rods 305 move in two parallel directions and in two opposite directions. However, the mobile rods 305 can move in a same direction. Furthermore, it is possible to form an angle between the mobile rods 305 of each elongation module, for example by inserting a flexible transmission shaft between the intermittent device 304 and the first end portion 321 of the threaded rod 302.

The two mobile rods 305 may or may not have identical lengths and sections.

The two intermittent devices are advantageously mounted in opposition. In other words, when one of the intermittent devices 304 is in the transmission state, the other intermittent device 304 is in the blocking state.

In particular, in the case where the intermittent devices 304 each comprise a Geneva wheel mechanism 310, they are mounted so that when the crescent-shaped lug 331 of one end of the control shaft 303 is positioned in a short notch 313 of a first Geneva wheel mechanism 310, the skewed lug 332 of the other end is in a long notch 314 of the second Geneva wheel mechanism 310, and vice versa.

The housing 306 forms a first part $C_1$, referred to as a reference part. Each mobile rod 305 forms a second part $C_2$ referred to as a transport part.

The connecting means, called connecting nuts, between the transport parts $C_2$, 305 and the threaded rods 303 are formed by the lenses 308, mounted on the threaded rods 302 and guided in rotation relative to the reference part 306, $C_1$.

The means for converting the movement of the connecting nuts into a movement of the transport parts 305, $C_2$ are formed by a rigid connection between said connecting nuts and the transport parts, for example by forcibly mounting the ends 351 of the rods 305 in an opening of the lenses 308.

The first axial abutment $C_{11}$ and the second axial abutment $C_{12}$ of each threaded rod 302 are formed by the nut 311 and the Geneva wheel mechanism 310 placed against the bearings $A_{11}$ and $A_{12}$ respectively formed by the recess 368 and the wall 367 of the housing $C_1$, 306.

The intermittent device 304 advantageously makes it possible to introduce a reduction ratio between the control shaft 303 and the threaded rods 302. For a complete revolution of the control shaft 303, the threaded rods 302 only perform part of a revolution, the value of which depends on the number of notches of the Geneva wheel mechanism 310.

The distraction rod 30 with two mobile rods 305 operates as follows.

The distal end portion 352 outside the housing 306 of a first mobile rod 305 is secured to part of a bone of a patient's limb or to a bone. The distal end portion 352 outside the housing 306 of the second mobile rod 305 is in turn fastened to another part of the bone, or another bone.

The patient's limb is then placed in a rotating magnetic field under the effect of which the magnet rotates the control shaft 303. A first half-revolution of the control shaft 303 causes a mobile rod 305 to move, then the second half-revolution causes the second mobile rod 305 to move.

This arrangement makes it possible for all of the torque of the control shaft 303 to be applied on each of the two threaded rods 302, each in turn.

The threaded rods 302 work exclusively in traction, whether they work to compress or distract the spine or the thorax.

Particularly when the search for a minimal bulk of the device has led to a device capable only of producing a small distraction or compression force, it is advantageous to leave translational play either between the threaded rod 302 and the housing $C_1$, 306 or between said tapped part that cooperates with the threaded rod 302 and the lens 308. In this way, it will be possible to facilitate the elongation of the distraction rod, by manipulating the patient from the outside, for example by grasping the patient under the shoulders to manually stretch the spine at the same time a torque is applied on the magnet, then releasing the patient, and so on. Upon each stretching, due to the translational play, the threaded rod will temporarily have no load and will therefore spontaneously rotate under the effect of the torque applied to the magnet moving the lens 308, thereby prohibiting the mobile rod 305 from resuming its initial position when the stretching is released. In this method, the rod 30 no longer produces the distraction or compression, but maintains that obtained through an external manipulation.

We will now refer to FIGS. 19 to 26, showing a fourth embodiment.

The distractor 40 shown in FIGS. 16 to 26 comprises a threaded rod 402, a control shaft 403, a transmission joint 404 between the threaded rod 402 and the control shaft 403.

The transmission joint 404 is for example formed by a chain of Cardan joints.

The distractor 40 comprises two mobile rods 405.

The threaded rod 402 and the control shaft 403 are not coaxial. In the illustrated embodiment, the axis of rotation of the threaded rod 402 is substantially parallel to the axis of rotation of the control shaft 403. The mobile rods 405 are mounted slidingly, inside a housing 406, the sliding axes of these mobile rods 405 being positioned substantially in the plane containing the axes of rotation of the threaded rod 402 and the control shaft 403.

In the illustrated embodiment, the threaded rod 402 extends between and substantially mid-distance from the sliding axes of the mobile rods 405.

The threaded rod 402 comprises two smooth end portions 421, 422 on either side of a threaded portion 423.

The control shaft 403 assumes the form of a hollow cylinder, in which a magnet is secured, for example using a silicone-based adhesive. At each of its ends, the control shaft comprises an axial lug 431, 432.

The mobile rods 405 each comprise a proximal end portion and a distal end portion. The terms "distal" and "proximal" are used here in reference to the housing 406.

The distal end portion 452 of each mobile rod 405 is capable of receiving connecting means (not shown) such as hooks, screws, or tapes, for fastening to the bones (in particular vertebrae, ribs, or pelvis) to which one wishes to attach it.

In the illustrated embodiment, the mobile rods 405 are substantially straight and parallel and can be cut and curved by the surgeon. In other embodiments not shown, at least one of these mobile rods 405 can be provided arched.

As appears in the figures, the two mobile rods 405 extend substantially symmetrically on either side of the threaded rod 402.

A connecting nut 408 is mounted on the threaded rod 402 while being guided in rotation relative to the reference part $C_1$, 406. This connecting nut 408 ensures the connection between the transport parts $C_2$, 405 and the threaded rod 402. This connecting nut 408 is provided with two recesses 409, 410 with opposite openings.

The housing 406 is formed by a primary shell 461, two end plates 462, 463, and a shell 464.

The primary shell 461 comprises a first substantially cylindrical conduit 465, housing the control shaft 403. The primary shell 461 comprises a second conduit 466 with three lumens. A first mobile rod 405a is slidingly mounted in a first lumen 467. A second mobile rod 405b is slidingly mounted in a second lumen 468. The connecting nut 408 is slidingly mounted in a third lumen 469.

The first end plate 462 is provided with a first opening 470 for the passage of a lug 431 of the control shaft 403. This lug 431 thus passes through the first end plate 462 and is assembled to the transmission joint 404. The first end plate 462 is provided with a second opening 471 through which the second mobile part 405b slides in a direction F1. The first end plate 462 is also provided with a third opening 472 for mounting an end portion 421 of the threaded rod 402. This end portion 421 passes through the first end plate 462 and is assembled to the transmission joint 404.

The second flange 463 is provided with a first opening 473 for the passage of a lug 432 of the control shaft 403. The second flange 463 is provided with a second opening 474 for mounting an end portion 422 of the threaded rod 402. The second flange 463 is also provided with a third opening 475 through which the first mobile part 405a slides.

A first nut 411 forms a first abutment $C_{11}$ against the first end plate 462, said first end plate 462 forming a first bearing $A_{11}$ to longitudinally block the threaded rod 402.

A second nut 412 forms a second stop $C_{12}$ against the second end plate 463, said second end plate 463 forming a second bearing $A_{12}$ to longitudinally block the threaded rod 402.

The first mobile part 405a is provided, at the proximal end portion 451 thereof, with a through hole 453 for the passage of a first pawl mechanism 455.

The second mobile part 405b is also provided, at the proximal end portion 451 thereof, with a through hole 456 for the passage of a second pawl mechanism 457.

The first pawl mechanism 455 comprises a pawl 458 that is mobile against an elastic means such as a spring, not shown, said pawl being provided with a detente ramp 460.

The second pawl mechanism 457 comprises a pawl 459, said pawl 459 being mobile against an elastic means such as a spring, not shown.

On each of the two mobile parts 405a, 405b, a ring 480 is advantageously welded, making it possible to easily view the movement performed on an x-ray.

Figure 22:
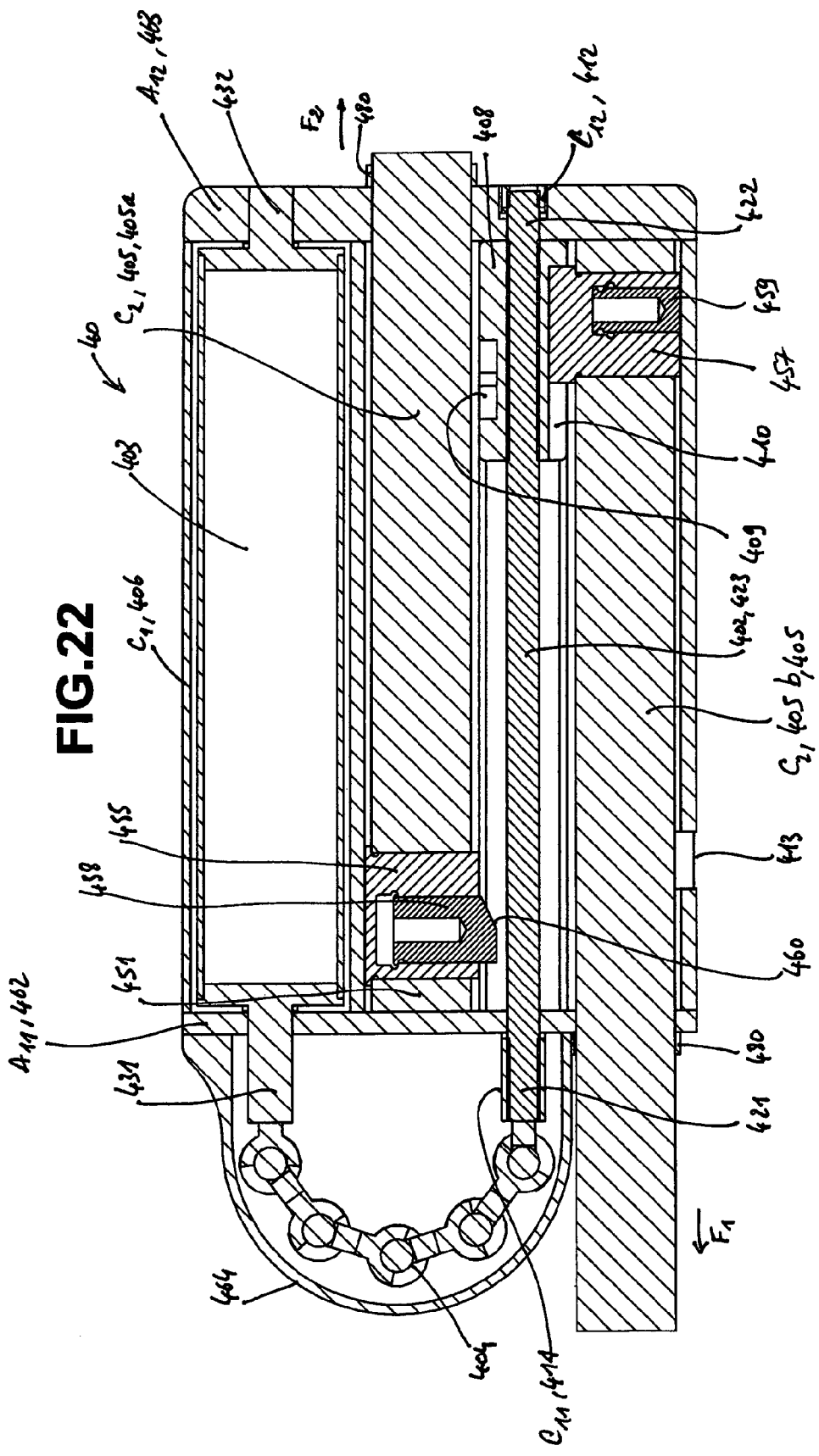
FIGS. 22 to 26 are cross-sectional views of the device of FIG. 19, in five different positions.

In a first extreme position, shown in FIG. 22, the second pawl mechanism 457 is abutting in a recess 410 of the connecting nut 408.

The rotation of the control shaft 403 is transmitted to the threaded rod 402 by the transmission joint 404. The rotation of the threaded rod 402 causes the connecting nut 408 to move.

Figure 23:
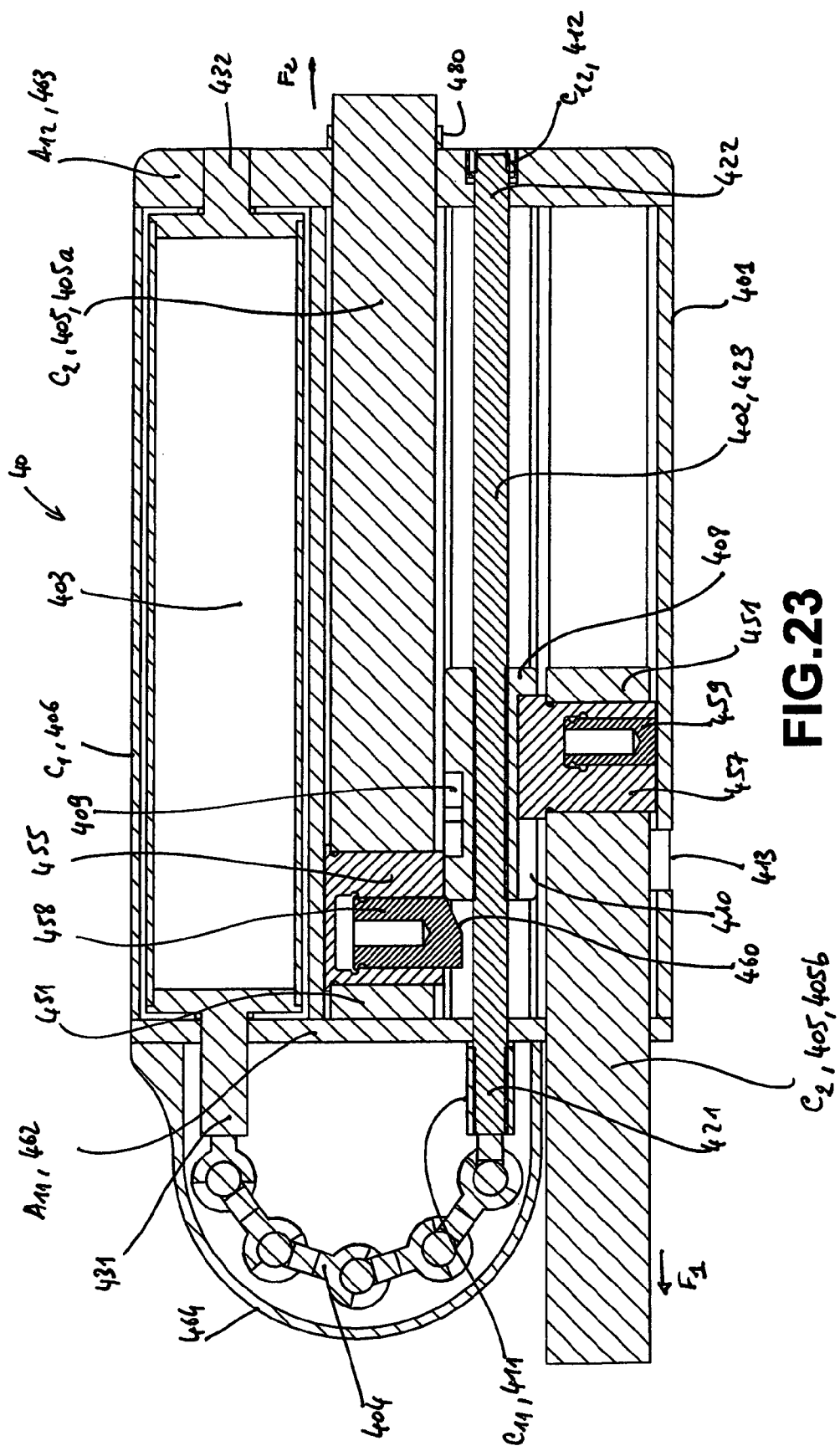
Figure 24:
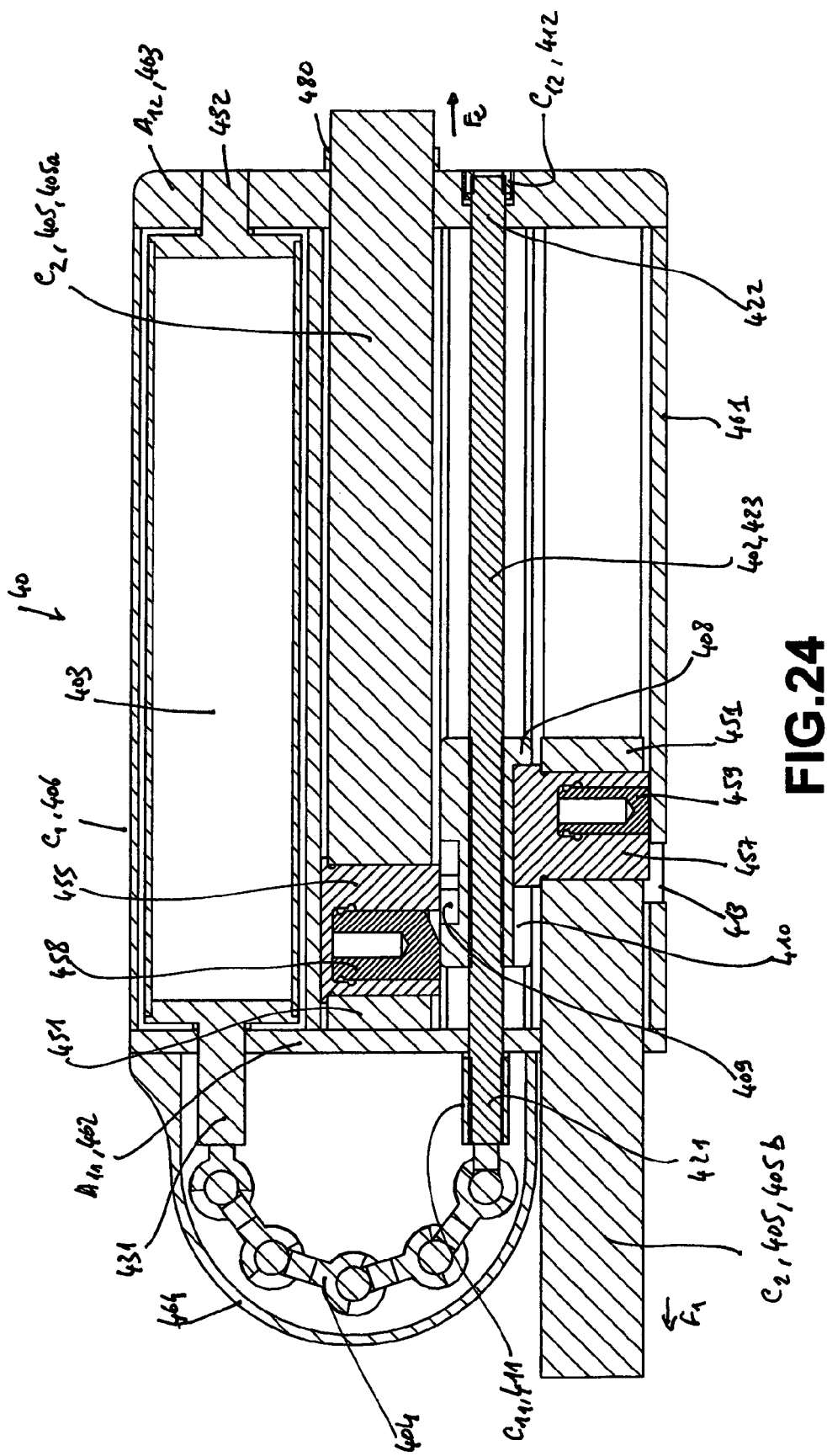
Figure 25:
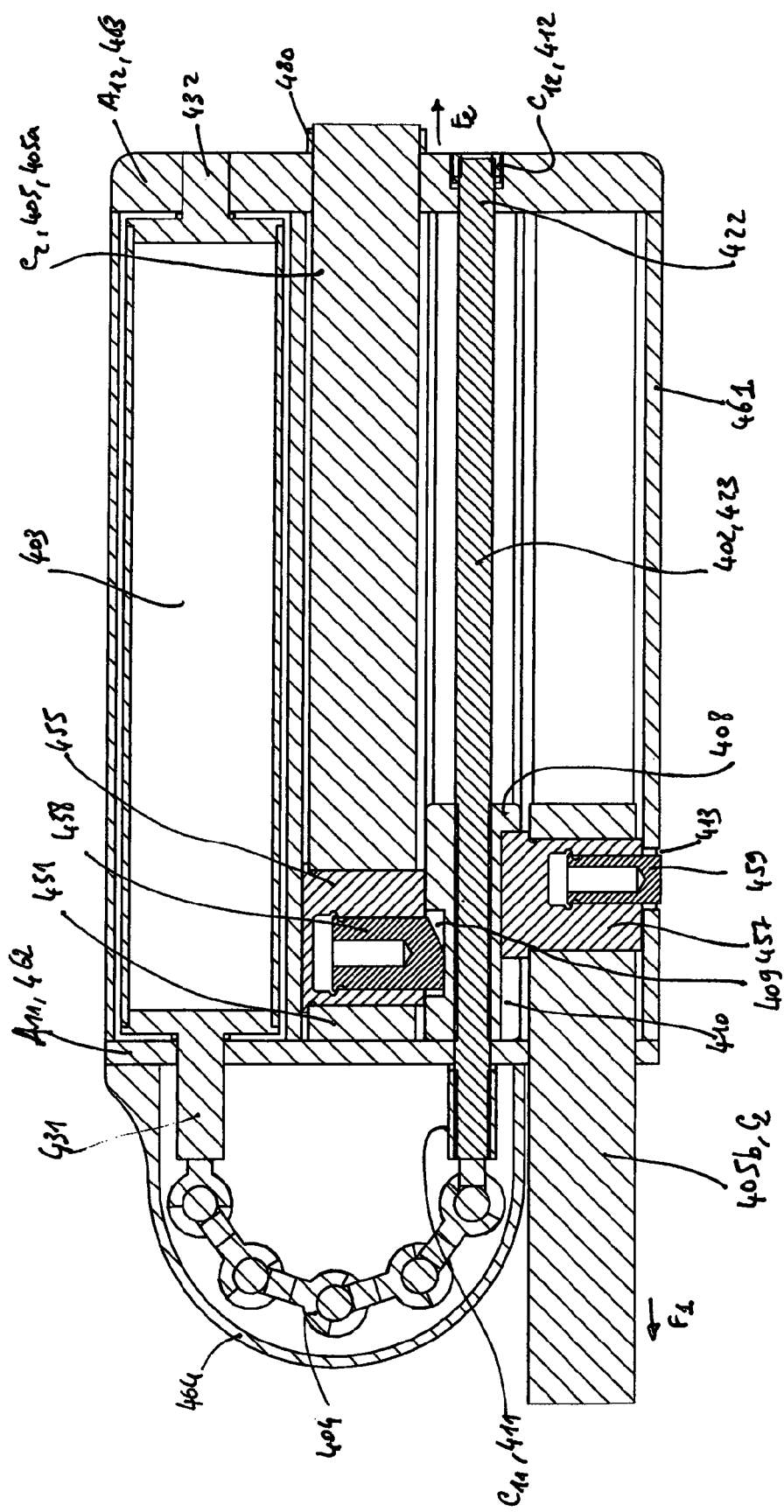

The movement of the connecting nut 408 drives the sliding out of the second mobile part $C_2$, 405b, in direction F1, from the extreme pushed-in position of said transport part $C_2$, 405b, shown in FIG. 22, to its extreme out position shown in FIG. 25, two intermediate positions being shown in FIGS. 23 and 24.

When the second transport part $C_2$, 405b is in the extreme out position, the pawl 459 of the second pawl mechanism 457 becomes housed in a recess, for example a through hole 413, of the reference part $C_1$, 406. This state is illustrated in FIG. 25. The outward movement of the pawl 459 is for example caused by a compression spring, not shown.

Advantageously, when the pawl 459 associated with the second transport part 405b is in the out position and blocked relative to the reference part $C_1$, 406, the pawl 458 associated with the first transport part 405a is housed in the recess 409 of the connecting nut 408 and the first transport part 405a is in the extreme pushed-in position. The detente ramp 460 facilitates the entry of the pawl 458 in abutment in the recess 409 of the nut 408.

Figure 26:
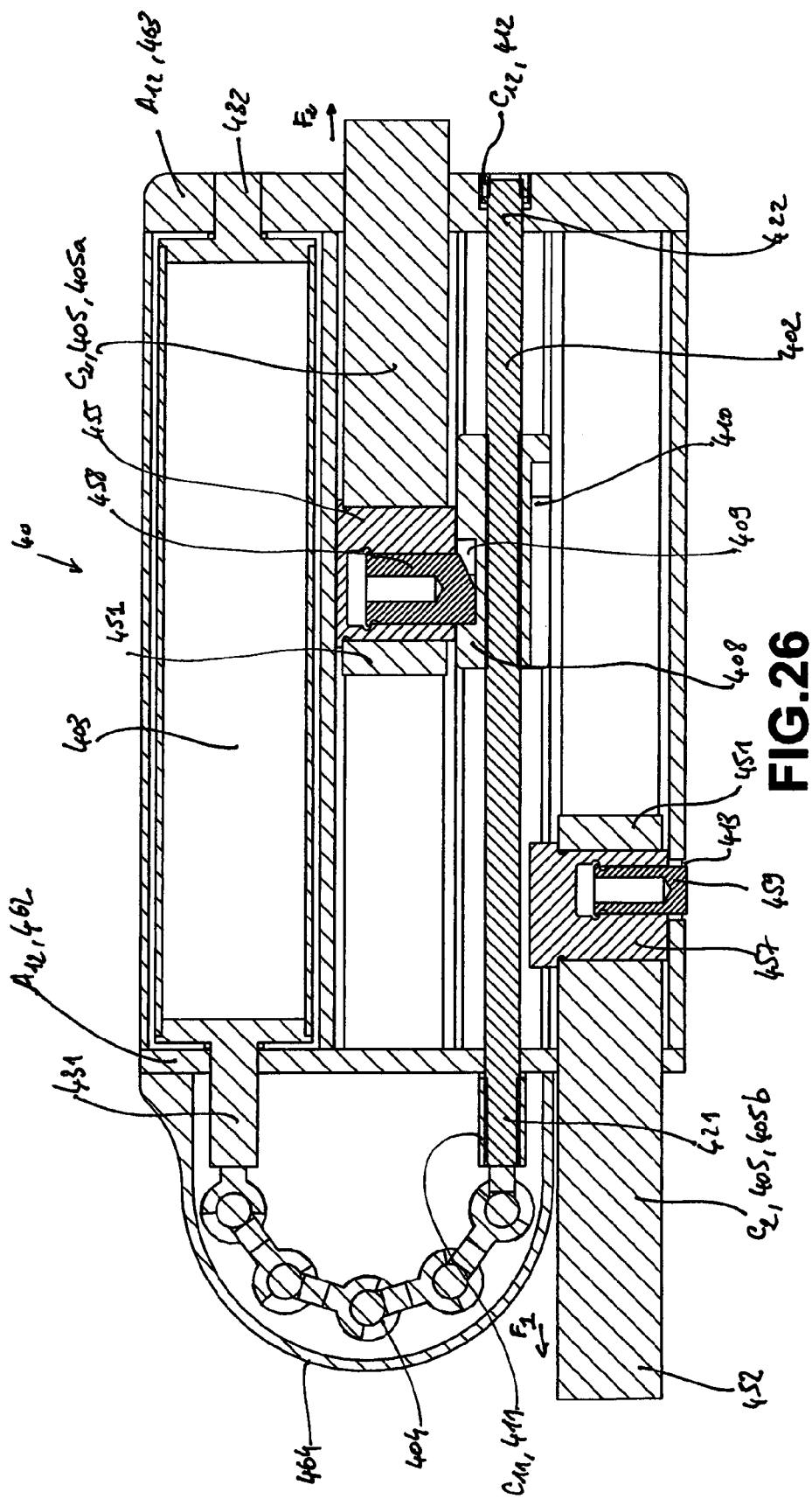

In this way, a rotational movement of the control shaft 403 causes the outward movement of the first transport part 405a, in direction F2, from its extreme pushed-in position, shown in FIG. 25, to its extreme out position (not shown), an intermediate position being shown in FIG. 26. During the outward movement of the first transport part 405a, the second transport part 405b stays in position, through locking of the pawl 459 in the recess 413 of the housing 406.

The housing 406 forms a first part $C_1$, called a reference part, the mobile rods 405a, 405b form two transport parts $C_2$, the abutments $C_{11}$ and $C_{12}$ of the threaded rod 402 are formed by the axial abutment nuts 411, 412 placed against the bearings $A_{11}$ and $A_{12}$ respectively formed by the end plates 462, 463 of the housing $C_1$, 406.

The connecting means between each transport part 405a, 405b and the threaded rod 402 is formed by a connecting nut 408 mounted on the threaded rod 402 and guided in rotation relative to the reference part 406, $C_1$.

The means for converting the movement of said connecting nut 408 into a movement of each transport part 405a, 405b comprise two pawls 458, 459, which advantageously have similar structures.

This preferred embodiment of the invention offers a substantial elongation potential in a particularly compact volume, and also allows the successive control of the mobile rods 405a, 405b.

In the described embodiments, the control is done using a magnet incorporated into the device. Advantageously, this magnet is a neodyme magnet having an admissible operating temperature of approximately 150° C. to allow the sterilization of said device using any means, and in particular steam heated to 134° C., without risk of deterioration of said permanent magnet.

A rotation of the magnet can be obtained easily by bringing a magnetic dipole of the magnet close to it, which acts through the corporeal tissue of the patient. When the dipole has performed a complete revolution, the magnet will also have performed complete revolution. In this way, no part of the device protrudes outside the patient's body.

Gear trains can be inserted between the control shaft and the transmission shaft, and/or between the transmission shaft and the threaded rod, so as to produce reduction ratios between the control and the threaded rod. In the event a single magnet controls two mobile rods, different reduction ratios can advantageously allow distinct, but proportional movements in both directions.

The devices presented make it possible to move tissue, in the direction of a distraction or a compression, or alternating between the two, implementing a limited number of parts.

The use of a flexible transmission shaft making it possible to do away with the alignment of the control shaft with the threaded rod, the general shape of the device can better adapt to the shape of the tissue in which it is implanted.

The flexible shaft also makes it possible to have a bidirectional device if it is rigidly connected at both of its ends, or to use one of its ends as a friction spring that will thus make it possible to rotate the threaded rod in one direction, i.e. the direction tending to tighten the spring, but not in the opposite direction, in which the spring will slip.

A complementary system for blocking the rotation in one direction may potentially be introduced, for example using springs or rolling bearings. Examples of such blocking systems are provided in documents U.S. Pat. No. 5,505,733 and WO 2004/019796.

The use of the threaded rod 2, 202, 302, 402 in traction makes it possible to eliminate the influence of buckling on the dimensioning of the rod. It is therefore possible to reduce the diameter of the threaded rod relative to devices working in compression.

The device according to the invention is advantageously made from mechanically resistant materials that are well tolerated by the body, such as stainless steels like 316L, titanium alloys, polymers such as Poly-Ether-Ether-Ketone (PEEK) or, preferably, high-performance chrome-and cobalt-based alloys such as, for example, the austenitic alloy marketed by the company Arcelor Mittal under the name PHYNOX (AFNOR designation: K13C20N16Fe15D07) or Nickel and Cobalt such as the VALLOY-120 specific to the EFAB method.

Furthermore, the surfaces of said device subject to friction, in particular the threaded rod, can advantageously receive an anti-wear surface treatment and/or a treatment decreasing their coefficient of friction with a base of amorphous diamond-like carbon or tungsten bisulfide, for example.

Thus, the combination of the small diameter of the threaded rod, made possible by its traction work, and the low coefficient of friction obtained owing to said surface treatments, makes it possible to drive the threaded rod using a modest torque in light of the load applied and also makes it possible to use simple means to create that torque, such as a transmission by permanent magnets of forces applied directly by hand.

The diameter of the threaded rod 2, 202, 302, 402 is commonly comprised between one and three millimeters and does not exceed four millimeters for a prosthesis in adult patients, for example.

The device according to the invention can advantageously be made without assembly, for example using the EFAB technique, proposed by the company Microfabrica, with the exception of a first door in the reference part and a second door in the structure surrounding the magnet, these doors allowing the insertion and adhesion of the magnet. This embodiment will be particularly advantageous for maxillofacial and cardiac applications, and surgery by hand using the device according to the invention, which require extreme compactness.

POSSIBILITIES FOR INDUSTRIAL APPLICATION

The device according to the invention is particularly useful in particular to produce rods to correct the spine of the thorax, lengthening or bone transport nails and plates, and growth prostheses.

The devices according to the invention are also applicable in the elongation or extension or the deformation of the soft tissue such as part of the intestine, or for artery banding, valvuloplasty rings with an evolutive geometry, and gastric bands.

The invention claimed is:

1. A device for moving tissue inside the body, in particular bone tissue, said device including:
   a reference part;
   a transport part which is slidably mounted relative to the reference part;
   a threaded rod comprising at least one thread, the threaded rod being pivotably mounted relative to the reference part;
   a control shaft;
   driving means connecting the control shaft to the threaded rod;
   a connecting nut linking the transport part and the threaded rod, the connecting nut being mounted onto the threaded rod and being rotatably guided relative to the reference part; and
   means for converting the movement of the connecting nut along the threaded rod into a movement of the transport part relative to the reference part;
   wherein in order to limit longitudinal translation of the threaded rod relative to the reference part, a first abutment and a second abutment rigidly connected to the threaded rod respectively cooperate with a first bearing and a second bearing, these bearings being rigidly connected to the reference part and being placed at a distance from one another between the first abutment and the second abutment, the connecting nut being movable along the threaded rod between the first bearing and second bearing.

2. The device according to claim 1, wherein the driving means comprises at least one helical spring.

3. The device according to claim 1, wherein the driving means comprises an intermittent device rigidly connected to the threaded rod and moved by the control shaft, the intermittent device being capable of converting a continuous rotational movement of the control shaft into an intermittent movement of the threaded rod.

4. The device according to claim 3, wherein the driving means comprises a Geneva wheel mechanism rigidly connected to the threaded rod.

5. The device according to claim 1, wherein the means for converting the movement of the connecting nut along the threaded rod into a movement of the transport part relative to the reference part comprises a rigid connection between the connecting nut and the transport part.

6. The device according to claim 5, wherein the connecting nut is rotationally guided relative to the reference part by a helical guide such that the connecting nut rotates by an angle of between 10 degrees and 180 degrees when it moves from the first bearing to the second bearing, or vice versa.

7. The device according to claim 1, further comprising a second transport part and a second threaded rod.

8. The device according to claim 7, wherein the threads of the two threaded rods have different diameter, direction, or pitch characteristics.

9. The device according to claim 1, wherein the diameter of the threaded rod is smaller than 4 mm.

10. The device according to claim 7, wherein the transport parts are controlled by a shared control shaft.

11. The device according to claim 1, further comprising connecting means for connecting the transport part to bone.

12. The device according to claim 1, characterized in that the control shaft comprises a permanent magnet whereof the direction of magnetization is substantially perpendicular to the axis of rotation of the control shaft.

* * * * *